United States Patent
Strobel et al.

(10) Patent No.: US 12,365,867 B2
(45) Date of Patent: Jul. 22, 2025

(54) RAPID ISOLATION, CULTIVATION METHODS AND UTILITIES OF TRUFFLE FUNGI

(71) Applicant: Black Boar Truffle, LLC, Bozeman, MT (US)

(72) Inventors: Gary A. Strobel, Bozeman, MT (US); Kelly W. Gaisford, Bozeman, MT (US)

(73) Assignee: BLACK BOAR TRUFFLE, LLC, Bozeman, MT (US)

( * ) Notice: Subject to any disclaimer, the term of this patent is extended or adjusted under 35 U.S.C. 154(b) by 0 days.

(21) Appl. No.: 18/621,769

(22) Filed: Mar. 29, 2024

(65) Prior Publication Data

US 2024/0327779 A1  Oct. 3, 2024

Related U.S. Application Data

(60) Provisional application No. 63/455,304, filed on Mar. 29, 2023.

(51) Int. Cl.
   *C12N 1/14* (2006.01)
(52) U.S. Cl.
   CPC .......... *C12N 1/145* (2021.05); *C12N 2500/34* (2013.01); *C12N 2500/76* (2013.01)
(58) Field of Classification Search
   None
   See application file for complete search history.

(56) References Cited

U.S. PATENT DOCUMENTS

| | | | |
|---|---|---|---|
| 9,277,760 B2 * | 3/2016 | Splivallo | ............... A23L 27/10 |
| 2012/0100255 A1 | 4/2012 | Splivallo | |
| 2017/0295837 A1 | 10/2017 | Soni | |
| 2020/0163333 A1 | 5/2020 | Gandhi | |

FOREIGN PATENT DOCUMENTS

| | | |
|---|---|---|
| JP | 2012143170 | 8/2012 |
| WO | 2020146650 | 7/2020 |

OTHER PUBLICATIONS

Sahab et al. Annals of Agricultural Science, 1984, vol. 29, No. 2, pp. 1069-1078.*
Rivera et al. "Selection of a decontamination treatment for fresh Tuber aestivum and Tuber melanosporum truffles packaged in modified atmospheres". Food Control, 2011, 22, pp. 626-632.*
Nowak, Z., Truffle: A Global History, Reaktion Books, 2015.
De Aza, C. et al., Fungal and bacterial communities in Tuber melanosporum plantations from northern Spain, Forests, 2022 13: 385.
Cullere, L. et al., Characterization of aroma active compounds in black truffles (Tuber melansporum) and summer truffles (Tuber aestivum) by gas chromatography-olfactometry, Food Chemistry 122, 2010, 300-306.
Strobel, G. A. et al., Volatile antimicrobials from a Novel Endophytic Fungus, Microbiology, 2001, 147, 2943-2950.
Saxena, S. et al., Marvelous Muscodor spp.: update on their biology and applications, Microbial Ecology, 2021, 82: 5-20.
Mitchell, A.M. et al., Volatile antimicrobials from Muscodor crispans, a novel endophytic fungus, Microbiology, 2010, 156: 270-277.
Urban, A. et al., Molecular studies on terricolous microfungi reveal novel anamorphs of two Tuber species, Mycol. Res. 108 (7), 2004, 749-758.
Iotti, M. et al., Morphological and molecular characterization of mycelia of some Tuber species in pure culture, New Phytologist, 2002, 155: 499-505.
White, T.J., Amplification and Direct Sequencing of Fungal Ribosomal RNA Genes for Phylogenetics, PCR Protocols: A Guide to Methods and Applications, 1990, 315-322.
Mustafa, A.M. et al., An overview of truffle aroma and main volatile compounds, Molecules, 2020, 25: 5948, https://doi.org/10.3390/molecules25245948.
Vahdatzadeh, M. et al., The Role of the Microbiome of Truffles in Aroma Formation: A Meta-Analysis Approach, Applied and Environmental Microbiology, 2015, 81: 6946-6952.
GenBank: OQ372947.1, Geotrichum candidum isolate Gc_07 internal transcribed spacer 1, partial sequence; 5.8Sribosomal RNA gene and internal transcribed spacer 2, complete sequence; and largesubunit ribosomal RNA gene, partial sequence:, Retrieved from https://www.ncbi.nlm.nih.gov/nucleotide/OQ372947.1?report=genbank&log$=nuclalign&blast_rank=2&RID=5ZJWN773013, (Feb. 9, 2023).

\* cited by examiner

*Primary Examiner* — Vera Afremova
(74) *Attorney, Agent, or Firm* — FULLER IP LAW LLC; Scott H. Blackman

(57) ABSTRACT

Methods of farming, domesticating, or cultivating truffle fungi, including isolation and cultivation methods for producing pure truffle fungi, or mini-truffles, typically a *Tuber* spp. or an *Iamai* spp. Examples of truffle include *Tuber melanosporum, Tuber magnatum, Tuber aestivum, Tuber uncinatum, Tuber borchii, Imaia* spp., *Tuber macrosporum, Tuber gibbosum, Tuber oregonense*, and *Tuber lyonii*. The isolated pure truffle may then be cultivated on a nutrient substrate, which may be, for example, a fruit, nut, grain, or a portion thereof, resulting in a truffle-flavored food product. Non-limiting examples of such substrates include rye, barley, lentil, wheat, rice, soybeans, pecan, hazelnut, pine nut, English walnut, coffee beans, mustard, cacao, sesame, sunflower, grapes, blackberries, blueberries, cherries, kiwi, mango, raspberries, and huckleberries.

19 Claims, 15 Drawing Sheets
(9 of 15 Drawing Sheet(s) Filed in Color)
Specification includes a Sequence Listing.

SEQUENCE LISTING

```
Sequence total quantity: 5
SEQ ID NO: 1              moltype = DNA  length = 507
FEATURE                   Location/Qualifiers
source                    1..507
                          mol_type = genomic DNA
                          organism = Tuber melanosporum
SEQUENCE: 1
cctgtgacat acctattgtt gcttcggcgg gatcgcccccg gcgccctcgg gcccggaccc  60
aggcgcccgc cggaggaccc aaactcttgt cttcatgaga atcttctgag taacacaagc 120
aaataaatta aaactttcaa caacggatct cttggttctg gcatcgatga agaacgcagc 180
gaaatgcgat aagtaatgtg aattgcagaa ttccgtgaat catcgaatct ttgaacgcac 240
attgcgcccg ccagtattct ggcgggcatg cctgttcgag cgtcatttca accctcaagc 300
ccccgggctt ggtgttgggg atcggccgcc ctccggcgcg ccggccccga aatctagtgg 360
cggtctcgct gtagcctcct ctgcgtagta acacacctcg caccggaacg cagcctggcc 420
acgccgttaa acccccccact tctgaaggtt gacctcggat caggtaggaa tacccgctga 480
acttaagcat atcaataagc ggaggaa                                     507

SEQ ID NO: 2              moltype = DNA  length = 494
FEATURE                   Location/Qualifiers
source                    1..494
                          mol_type = genomic DNA
                          organism = Tuber magnatum
SEQUENCE: 2
ccctgtgaca taccatattg ttgcctcggc ggtgcctgtt tcggcagccc gccagaggac  60
ccaaacccta gattacatta aagcattttc tgagtcaatg attaaatcaa tcaaaacttt 120
caacaacgga tctcttggtt ctggcatcga tgaagaacgc agcgaaatgc gataagtaat 180
gtgaattgca gaattcagtg aatcatcgaa tctttgaacg cacattgcgc ccgcagtat  240
tctggcgggc atgcctgtcc gagcgtcatt tcaaccctca agcccccggg cttggtgttg 300
gagatcggcg agcccccccgg ggcgcgccgt ctcccaaata tagtggcggt cccgctgtag 360
cttcctctgc gtagtagcac acctcgcact gggaaacagc gtggccacgc cgtaaaaccc 420
cccacttctg aaaggttgac ctcggatcag gtaggaatac ccgctgaact taagcatatc 480
aataagcgga ggaa                                                   494

SEQ ID NO: 3              moltype = DNA  length = 324
FEATURE                   Location/Qualifiers
source                    1..324
                          mol_type = genomic DNA
                          organism = Tuber aestivum
SEQUENCE: 3
gtganttaca cngcaacaat aattttatan tcaaanacnn aaaataatca aaacttttaa  60
caatggatct cttggttctc gtatcgatga agaacgcagc gaaacgcgat atttcttgtg 120
aattgcagaa gtgaatcatc agttttttgaa cgcacattgc actttggggt atccccaaa  180
gtatacttgt ttgagcgttg tttctctctt ggaattgcat tgcttttcta aaatttcgaa 240
tcaaattcgt ttgaaaaaca acactattca acctcagatc aagtaggatt acccgctgaa 300
cttaagcata tcaannngcg gagg                                        324

SEQ ID NO: 4              moltype = DNA  length = 482
FEATURE                   Location/Qualifiers
source                    1..482
                          mol_type = genomic DNA
                          organism = Tuber uncinatum
SEQUENCE: 4
actatatcca tctacacctg tgaaccgttt gattgaatct tctgattcaa ttttacaaac  60
attgtgtaat gaacgtcatt agatcataac aaaaaaaaac ttttaacaac ggatctcttg 120
gctctcgcat cgatgaagaa cgcagcgaaa tgcgataagt aatgtgaatt gcagaattca 180
gtgaatcatc gaatctttga acgcaacttg cgctctctgg tattccggag agcatgcctg 240
tttgagtgtc atgaaatctc aaccattagg gtttcttaat ggcttggatt tggaggttgc 300
cattctaaat ggctcctctt aaaggagtta gcaagtttta ctattgctat ctggcgtaat 360
aagtttcgct ggaatggtat tgtgaagcgt gcttctaatc gtcttcggac aattactttg 420
actctggcct caaatcaggt aggactaccc gctgaactta agcatatcaa taagcggagg 480
aa                                                                482
```

```
SEQ ID NO: 5            moltype = DNA  length = 313
FEATURE                 Location/Qualifiers
source                  1..313
                        mol_type = genomic DNA
                        organism = Tuber borchii
SEQUENCE: 5
ttgtgattta ccacagcaac aaaaatcata caatcaaaac aaaaataatt aaaactttta   60
acaatggatc tcttggttct cgtatcgatg aagaacgcag cgaaacgcga tatttcttgt  120
gaattgcaga agtgaatcat cagtttttga acgcacattg cactttgggg tatcccccaa  180
agtatacttg tttgagcgtt gtttctctct tggaattgct ttgctcttct aaaatttcga  240
atcaaattcg tttgaaaaac aacactattc aacctcagat caagtaggat tacccgctga  300
acttaagcat atc                                                    313
```

RAPID ISOLATION, CULTIVATION METHODS AND UTILITIES OF TRUFFLE FUNGI

RELATED APPLICATIONS

This application claims the benefit of U.S. provisional patent application 63/455,304, filed Mar. 29, 2023, to Gary A. Strobel, titled "Rapid Isolation, Cultivation and Novel Utilities of Truffle fungi (*Tuber* spp.)," the entirety of the disclosure of which is hereby incorporated by this reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 7,511 byte XML file named "22630.002US-PAT" created on Mar. 28, 2024.

TECHNICAL FIELD

This disclosure relates to methods of farming or domesticating truffle fungi. In some aspects, the disclosure relates to isolation and cultivation methods for producing pure truffle fungi.

BACKGROUND

The fruiting bodies of the truffle fungi have been sought after for thousands of years and are prized for their flavor making them extremely expensive in all markets. Most commonly, they are collected in the soil surrounding certain tree species and certain dogs and trained pigs are used to locate the prized truffles. Once located, the truffle is then dug from the soil and shipped for commercial distribution. The truffle itself ranges from about 1 to 6-8 or more cm in diameter with a rough and undulating surface and can be used for the enhancement of flavor in all types of foods.

Cultivation of the truffle has traditionally been done by dedicating land to certain tree types (usually oak species but others as well including pecan, and hazelnut) and then inoculating the roots of the trees being planted with harvested truffle material that carries spores and mycelial fragments that invade the young roots. Eventually the infected roots begin to support the growth of the fungus, which is attached to them, to produce a root enlargement that contains the truffle fungus, plant tissues and a plethora of soil related microbes. The fungal growth begins as a small ball of enlarged root growth eventually enlarging to the full-sized truffle. Full truffle development takes five to ten years.

The long processes involved in truffle production; their short shelf life once dug from the soil as well as the demand for the truffle itself add to the cost of this sought-after culinary delicacy. Given the multitude of costs and time involved in their production prices for truffle can be expensive (for example, $700-$1000/lb. or more for black truffle, and $3,000/lb. or more for white truffle).

To satisfy market demand, a method for farming truffles is needed.

SUMMARY OF THE DISCLOSURE

Growing truffles is a long and involved process that contributes to the high costs of this culinary delicacy. A method to grow and farm truffles would aid in lowering the cost associated with truffle production by increasing market availability without having to rely on the traditional collection methods to obtain the truffles.

The present disclosure is directed to a method of isolating and culturing truffle fungi species that provides an alternative for the domestication of major truffle species. The disclosure includes methods for growing commercially valuable truffles without the need for soil, therefore reducing the time needed for truffle production. The disclosure includes a method to isolate pure culture of ascomycetous fungus that can be grown on plates, such method provides an alternative to obtain inoculants free of soil-borne contamination.

Some embodiments of the present disclosure comprise a method of growing truffles comprising the steps of obtaining a spore-producing fruiting body of an ascomycetous fungus from soil, scraping the inside of the spore-producing fruiting body of the ascomycetous fungus to collect a fruiting body sample, placing the fruiting body sample on a first surface comprising a nutrient substrate, wherein the nutrient substrate comprises: a simple sugar, a botanical isolate and agar, incubating the fruiting body sample on the nutrient substrate with an antimicrobial volatile mixture until mycelium formation, wherein the presence of mycelium indicates new fungal growth; and transferring the new fungal growth into a second surface comprising the nutrient substrate to obtain a pure culture of the ascomycetous fungus.

Some embodiments of the present disclosure comprise soil-less method of growing truffle comprising the steps of obtaining a spore-producing fruiting body of an ascomycetous fungus from soil, scraping the inside of the spore-producing fruiting body of the ascomycetous fungus to collect a fruiting body sample, placing the fruiting body sample on a first surface comprising a nutrient substrate, incubating the fruiting body sample on the nutrient substrate with an antimicrobial volatile mixture until mycelium formation, and transferring the new fungal growth into a second surface comprising the nutrient substrate to obtain a pure culture of the ascomycetous fungus. Presence of mycelium indicates new fungal growth. In some embodiments of the present disclosure, the nutrient substrate comprises: a simple sugar; a botanical isolate; and agar.

In some aspects of the present disclosure, the ascomycetous fungus comprises a *Tuber* spp. and *Iamai* spp. In another aspect of the disclosure, the ascomycetous fungus is selected from a group consisting of: *Tuber melanosporum, Tuber magnatum, Tuber aestivum, Tuber uncinatum, Tuber borchii, Imaia* spp., *Tuber macrosporum, Tuber gibbosum, Tuber oregonense*, and *Tuber lyonii* (a/k/a *Tuber Texense*). In yet another aspect of the disclosure, the botanical isolate comprises a fruit, nut, grain, or a portion thereof.

In some embodiments of the present disclosure, the antimicrobial volatile mixture is derived from the volatile organic compounds produced by a *Muscodor* spp. organism. In some aspects, the antimicrobial volatile mixture comprises at least one of: Propanoic acid, 2-methyl-, methyl ester; Ethanol; Acetic acid, 2-methylpropyl ester; Propanoic acid, 2-methyl-, 2-methylpropyl ester; 1-Propanol, 2-methyl-; 2-Butenal, 2-methyl-, (E)-; 1-Butanol, 3-methyl-, acetate; Propanoic acid, 2-methyl-, 2-methylbutyl ester; 1-Butanol, 3-methyl-; Propanoic acid, 2-methyl-, or isobutyric acid; and Acetic acid, 2-phenylethyl ester.

In some embodiments, a nutrient substrate comprises potato dextrose agar. Other nutrient substrates may comprise pecan agar. In some embodiment of the disclosure, the second nutrient substrate may comprise a liquid. In some aspects, the nutrient substrate may comprise potato dextrose broth.

Another embodiment of the present disclosure comprises a method of growing mini-truffles. Some aspects comprise obtaining a spore-producing fruiting body of an ascomycetous fungus from soil, scraping the inside of the spore-producing fruiting body of the ascomycetous fungus to collect a fruiting body sample, placing the fruiting body sample on a first surface comprising a nutrient substrate, incubating the fruiting body sample on the nutrient substrate with an antimicrobial volatile mixture until mycelium formation, transferring the new fungal growth into second surface comprising the nutrient substrate to obtain a pure culture of the ascomycetous fungus, incubating the pure culture with fruit, nut, grain, or a portion thereof for at least week to produce an inoculated botanical sample, and placing the inoculated botanical sample on a third surface comprising the nutrient substrate to produce mini-truffles. In some aspects, the volatile organic compounds comprise compounds produced by a *Muscodor* spp. organism, for example, *Muscodor crispans*. The nutrient substrate may comprise dextrose agar, potato dextrose broth, and pecan agar, among some non-limiting examples. In yet another aspect of the present disclosure, the third surface may comprise pecan agar.

In yet another embodiment, the method of growing mini-truffles may further comprise incubating the pure culture with fruit, nut, grain, or a portion thereof for at least two weeks to produce an inoculated botanical sample, placing the inoculated botanical sample in a sugar solution for at least a week to produce inoculated sugar solution, and incubating inoculated sugar solution on a third surface comprising the nutrient substrate to produce mini-truffles. In some non-limiting examples, the third surface nutrient substrate comprises potato dextrose agar or pecan agar. In some non-limiting aspects of the disclosure, the sugar solution comprises honey or maple syrup. Some non-limiting examples of fruit, nut, grain, or a portion thereof include: rye, barley, lentil, wheat, rice, soybeans, pecan, hazelnut, pine nut, English walnut, coffee beans, mustard, cacao, sesame, sunflower, grapes, blackberries, blueberries, cherries, kiwi, mango, raspberries and huckleberries.

In still yet another embodiment, a method of making a truffle-flavored food product is herein disclosed. The method comprises incubating a pure culture of ascomycetous fungus with fruit, nut, grain, or a portion thereof for at least week to produce an inoculated botanical sample and processing the inoculated botanical sample into a food product. In one aspect of the embodiment, the processing step of the method comprises at least one of: grinding the inoculated botanical sample into a powder and creating a mash using the inoculated botanical sample. In another aspect of the present disclosure, the powder or mash is mixed with a food product. In some non-limiting examples of food products, the powder or mash is used to create salts, oils, dressings, spreads, and drinks.

Another embodiment disclosed herein comprises a method for storing a pure culture of ascomycetous fungus. In some aspects, the method comprises providing sterile water, adding the pure culture of ascomycetous fungus to the sterile water to produce an inoculated solution, and storing the inoculated solution in a controlled temperature condition of 1-5° C. In another embodiment, a method for storing a pure culture of ascomycetous fungus comprises: providing sterile medium selected from the group consisting of a nut or a portion thereof and a grain or a portion thereof, inoculating the sterile medium with the pure culture of ascomycetous fungus to produce an seed population of ascomycetous fungus; and storing the seed population of ascomycetous fungus in a controlled temperature condition. In some aspects of the disclosure, the controlled temperature condition is −80° C. to −20° C. In some other aspects of the disclosure, the controlled temperature condition is 20° C. to 25° C., the method further comprises drying the seed population of ascomycetous fungus.

In yet another embodiment, the present disclosure comprises a method of growing a known species of truffle. The method comprises obtaining a spore-producing fruiting body of an ascomycetous fungus from soil, scraping the inside of the spore-producing fruiting body of the ascomycetous fungus to collect a fruiting body sample, placing the fruiting body sample on a first surface comprising a nutrient substrate, wherein the nutrient substrate comprises: a simple sugar, a botanical isolate, and agar, incubating the fruiting body sample on the nutrient substrate with an antimicrobial volatile mixture until mycelium formation, wherein the presence of mycelium indicates new fungal growth, transferring the new fungal growth into second surface comprising the nutrient substrate and a sterile medium selected from the group consisting of: nut or a portion thereof and a grain or a portion thereof to obtain an inoculant, combining sterile water with the inoculant at a volume ratio 1 part inoculant to 4 parts water to produce a suspension, mixing the suspension with a soil mixture to produce a fungal soil mixture, applying the fungal soil mixture to a plant root or a portion thereof. In some aspects, the fungal soil mixture is air dried and stored at 3° C. In other aspects the fungal soil mixture is stored at −20° C., and at −80° C. The method may further comprise mixing the fungal soil mixture with the soil in the area where roots of host trees are growing, so as to inoculate with the pure culture of the ascomycetous fungus.

In an additional embodiment, a truffle-growing composition is disclosed herein. The composition comprises a grain and mycelium from a truffle species. In some aspects of the disclosure, the truffle species contains at least one of: SEQ ID NO: 1, SEQ ID NO: 2, SEQ ID NO: 3, SEQ ID NO: 4, or SEQ ID NO: 5 and the grain is infested with the truffle species.

The foregoing and other aspects, features, and advantages will be apparent from the DESCRIPTION and DRAWINGS, and from the CLAIMS if any are included.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A is a drawing representation of synnemata of the fungus *Tuber melanosporum*. The spores are each about 3 microns in diameter. FIG. 3B is a drawing representation of a close up of conidiospore production on the synnemata of *T. melanosporum*. The spores are 3-4 microns in dia. FIG. 3C an image illustrating a scanning electron micrograph of a 6-week-old black truffle culture (*Tuber melanosporum*). The micrograph shows the synnemata consisting of two or more fructiferous conidiophores that are intertwined and producing conidiospores mostly along their entire length. The conidiospores bud randomly from the surface of the conidiophores (see inset with spore buds at the base of the large conidiophore). The spores average 2.5-3.0 µm in length and the buds are about 0.5 µm in diameter.

DETAILED DESCRIPTION

Figure 1:
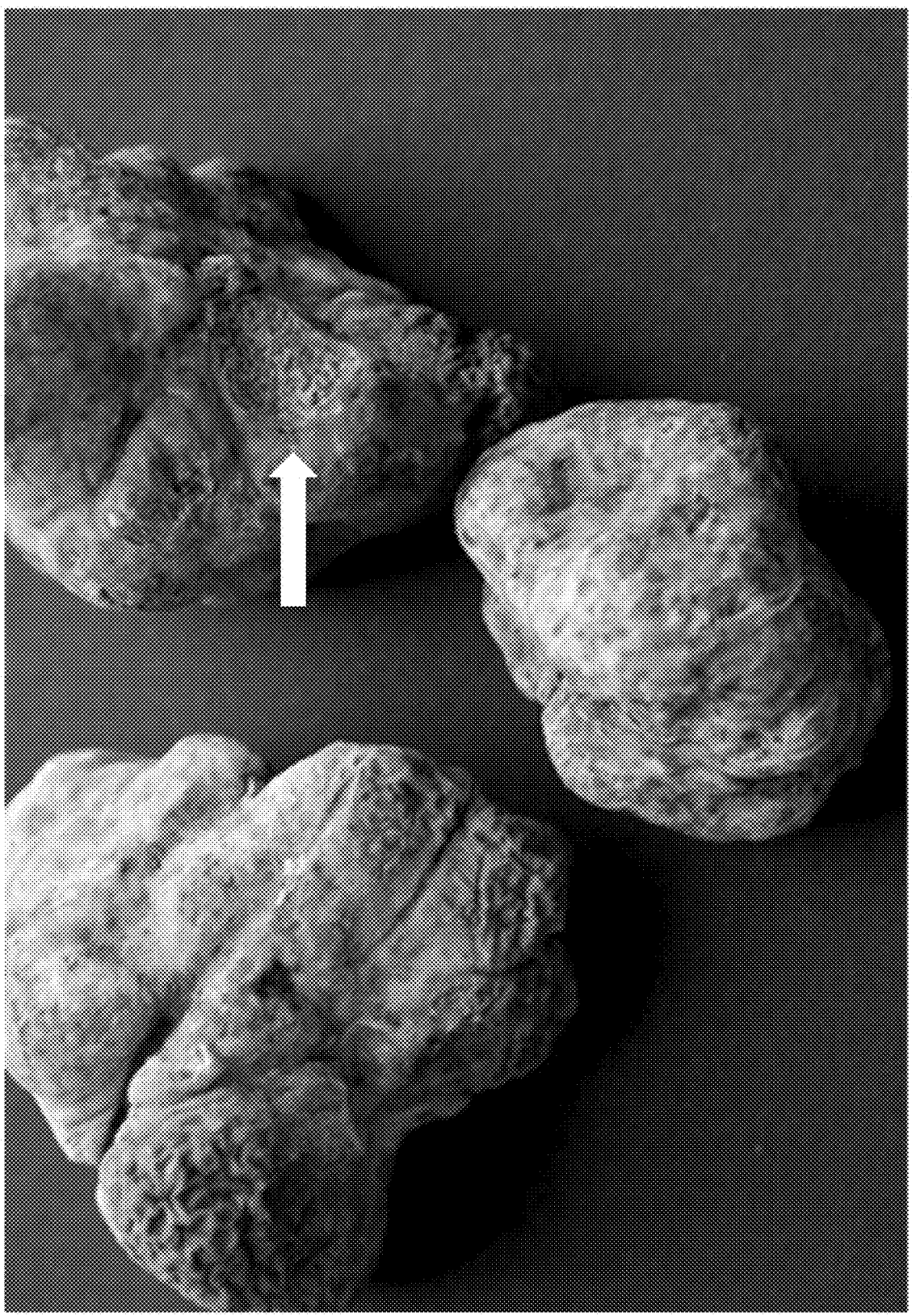
FIG. 1 is an image of freshly harvested white truffles *Tuber magnatum* representing the typical look of intact truffles and illustrating newly cut areas of the truffles (truffle in the upper right corner of the image; white arrow) for sampling and culturing purposes.

Detailed aspects and applications of the disclosure are described below in the following drawings and detailed description of the technology. Unless specifically noted, it is intended that the words and phrases in the specification and the claims be given their plain, ordinary, and accustomed meaning to those of ordinary skill in the applicable arts.

In the following description, and for the purposes of explanation, numerous specific details are set forth in order to provide a thorough understanding of the various aspects of the disclosure. It will be understood, however, by those skilled in the relevant arts, that embodiments of the technology disclosed herein may be practiced without these specific details. It should be noted that there are many different and alternative configurations, devices and technologies to which the disclosed technologies may be applied. The full scope of the technology disclosed herein is not limited to the examples that are described below.

The singular forms "a," "an," and "the" include plural referents unless the context clearly dictates otherwise. Thus, for example, reference to "a step" includes reference to one or more of such steps.

The words "exemplary," "example," or various forms thereof are used herein to mean serving as an example, instance, or illustration. Any aspect or design described herein as "exemplary" or as an "example" is not necessarily to be construed as preferred or advantageous over other aspects or designs. Furthermore, examples are provided solely for purposes of clarity and understanding and are not meant to limit or restrict the disclosed subject matter or relevant portions of this disclosure in any manner. It is to be appreciated that a myriad of additional or alternate examples of varying scope could have been presented but have been omitted for purposes of brevity.

When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

Throughout the description and claims of this specification, the words "comprise" and "contain" and variations of the words, for example "comprising" and "comprises", mean "including but not limited to", and are not intended to (and do not) exclude other components.

As required, detailed embodiments of the present disclosure are included herein. It is to be understood that the disclosed embodiments are merely exemplary of the invention that may be embodied in various forms. Therefore, specific structural and functional details disclosed herein are not to be interpreted as limits, but merely as a basis for teaching one skilled in the art to employ the present invention. The specific examples below will enable the disclosure to be better understood. However, they are given merely by way of guidance and do not imply any limitation.

The present disclosure may be understood more readily by reference to the following detailed description taken in connection with the accompanying figures and examples, which form a part of this disclosure. It is to be understood that this disclosure is not limited to the specific materials, devices, methods, applications, conditions, or parameters described and/or shown herein, and that the terminology used herein is for the purpose of describing particular embodiments by way of example only and is not intended to be limiting of the claimed inventions. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

More specifically, this disclosure, its aspects and embodiments, are not limited to the specific material types, components, methods, or other examples disclosed herein. Many additional material types, components, methods, and procedures known in the art are contemplated for use with particular implementations from this disclosure. Accordingly, for example, although particular implementations are disclosed, such implementations and implementing components may comprise any components, models, types, materials, versions, quantities, and/or the like as is known in the art for such systems and implementing components, consistent with the intended operation.

The present disclosure relates to methods of isolating and culturing truffle fungi species. The truffle fungi species described and utilized include a subterranean ascomycetous fungus of the genus *Tuber* spp. as well as *Imaia* spp. The methods described are useful for the domestication of truffle fungi species through isolation and culturing. The domestication of major truffle species has major implications for commercially valuable truffles in reducing the time needed for truffle production. Thus, methods of growing truffle that do not require the use of soil is disclosed. In some aspects, the method establishes a pure culture of truffle fungus. In some implementations, the method grows mini-truffles. In some aspects, the method grows a known species of truffle.

The methods disclosed provide an effective and useful procedure for the successful isolation of truffle fungi. Additionally, this disclosure describes a method for the successful storage of the pure isolated fungi cultures reducing the need for constant harvesting from soil. Furthermore, methods described herewith include the cultivation of pure truffle fungi cultures on natural as well as artificial substrates and the use of such cultures as inoculums for roots to propagate the truffle fungi in fields. Additionally, the pure isolated cultures obtained by these methods may be used to create novel food products such as beverages, spreads, salad dressing, seasoning, among many others.

There are many advantages in having each of the truffle fungi in pure culture which makes them available to make a wide range of novel food related products each holding a truffle fungal flavoring after growth on a particular food product such as a grain or nut or fruit. It is to be noted that we are not aware of any organization in the world having any of these fungi in pure culture being used for the preparation of any food product.

As noted above, the only available truffle products currently available anywhere are from natural sources involving the truffle itself. Normally, pieces of truffle or slices thereof are added to cuisine via freshly harvested or dried pieces of the harvested truffle itself. And that flavor is strictly limited in scope because the fungus had been growing and obtained from only one tree source. Now, depending upon the conditions and substrates in which a fungus is grown, the secondary products that it makes are dependent upon these nutrients available for growth. In other words, having a pure culture of a fungus, as per the truffle fungi, one can grow them on a multitude of substrates and under varying conditions and that will ultimately influence the flavoring of the products made by the fungus as it modifies its hosts biochemical components. This unique feature of fungal fermentation has been taken advantage of to discover a plethora of novel potential food products that are listed here forth.

One solution to the problems involved with acquiring truffles is the prospect of isolating the fungus and simply growing it either in liquid or solid-state fermentation in the laboratory. Such methods would drastically lower all costs, especially those related to the time frame for field production. This solution is ideal since there is no reason to believe that truffles from soil growing on tree roots can have any taste or nutritional value greater than the truffle fungus grown on sterile defined or natural substrates. Commercially, this feat has not been done anywhere in the world. One of the reasons for this lack of domestication is that these truffle fungi species are not available from state or national culture collections or from university culture collections. This is due to these fungi being exceedingly difficult to isolate in pure culture. Thus, if one wishes to have a local strain available for culturing it will be important and necessary to acquire the truffle and then proceed with fungal isolation.

One of the difficulties of the process of fungal isolation is that the truffle itself is surrounded by water which is contaminated with soil-loving bacteria, other fungi and organisms making the isolation processes difficult, and in most cases impossible. Also, all of the truffle species are extremely slow growing and are easily overtaken in growth by other contaminating fungi and bacteria that inhabit the ground dwelling truffle. A successful isolating method would mean all of the expense and time spent trying to grow and recover truffles from field inoculated trees would not be necessary. The truffle fungus could be increased and made available within a few weeks having been grown on a plethora of substrates including natural ones, each of which has the prospects of providing new products to the marketplace. The potential marketplace for these truffles and their products is huge. Examples of these types of products include food and beverage items, among many possible products.

A novel and unexpected solution to the problem of truffle-fungus isolation is presented in this disclosure. Described here forth are methods that show that the isolation of virtually all of the major truffle species can be accomplished relatively quickly by a cultural selection technique involving the use of a special cocktail of volatile organic substances (VOCs) that precludes the development of soil born microbes that act as contaminants of the truffle itself. The special cocktail of VOCs is based on the VOCs naturally produced by truffle fungi, which include alcohols, esters, aldehydes, ketones, aromatic compounds, furans, alkanes, terpenoids, and, most importantly, sulfur-containing compounds. However, one must be skilled in the art of mycology in order to completely and successfully carry out this novel procedure. Ultimately, once in hand, the individual truffle species can be grown on a selection of natural substrates including grains, nuts and berries resulting in an entirely novel series of useful, enticing, and tasteful products that each represents a useful and healthful addition to the food marketplace. Such possibilities are the result of having a pure culture of the fungus obtained by the methods disclosed here.

The method of growing truffle comprises obtaining a spore-producing fruiting body of an ascomycetous fungus from soil, scraping the inside of the spore-producing fruiting body of the ascomycetous fungus to collect a fruiting body sample, placing the fruiting body sample on a first surface comprising a nutrient substrate, incubating the fruiting body sample on the nutrient substrate with an antimicrobial volatile mixture until mycelium formation, and transferring the new fungal growth into a second surface comprising the nutrient substrate to obtain a pure culture of the ascomycetous fungus. The presence of mycelium indicates new fungal growth. In some embodiments of the present disclosure, the nutrient substrate comprises: a simple sugar; a botanical isolate; and agar. In certain implementations the nutrient substrate further comprises at least one protein component, for example peptone and/or yeast extract. In some aspects, the botanical isolate is fruit, nut, grain, or a portion thereof. In particular implementations, the nutrient substrate that is potato dextrose agar. In other implementations, the nutrient substrate is pecan agar. In some embodiment of the method, the second nutrient substrate comprises a liquid. In some aspects, the nutrient substrate comprises potato dextrose.

Another embodiment of the present disclosure comprises a method of growing mini-truffles. In some non-limiting examples, a mini-truffle comprises tightly knitted small round balls in the range of 2 mm in diameter—smaller than would normally be expected of wild truffles. Some aspects comprise obtaining a spore-producing fruiting body of an ascomycetous fungus from soil, scraping the inside of the spore-producing fruiting body of the ascomycetous fungus to collect a fruiting body sample, placing the fruiting body sample on a first surface comprising a nutrient substrate, incubating the fruiting body sample on the nutrient substrate with an antimicrobial volatile mixture until mycelium formation, transferring the new fungal growth into second surface comprising the nutrient substrate to obtain a pure culture of the ascomycetous fungus, incubating the pure culture with fruit, nut, grain, or a portion thereof for at least week to produce an inoculated botanical sample, and placing the inoculated botanical sample on a third surface comprising the nutrient substrate to produce mini-truffles. The volatile organic compounds comprise compounds produced by a *Muscodor* spp. organism. The nutrient substrate comprises potato dextrose agar, potato dextrose broth, and pecan agar, among some non-limiting examples. In yet another aspect of the present disclosure, the third surface is pecan agar.

In yet another embodiment, the method of growing mini-truffles further comprises incubating the pure culture with fruit, nut, grain, or a portion thereof for at least week to produce an inoculated botanical sample, placing the inoculated botanical sample in a sugar solution for at least a week to produce inoculated sugar solution, and incubating inoculated sugar solution on a third surface comprising the nutrient substrate to produce mini-truffles. In some non-limiting examples, the third surface nutrient substrate comprises potato dextrose or pecan agar. In some non-limiting aspects of the disclosure, the sugar solution comprises honey or maple syrup. Some non-limiting examples of fruit, nut, grain, or a portion thereof include: rye, barley, lentil, wheat, rice, soybeans, pecan, hazelnut, pine nut, English walnut, coffee beans, mustard, cacao, sesame, sunflower, grapes, blackberries, blueberries, cherries, kiwi, mango, raspberries, and huckleberries.

In yet another embodiment, the present disclosure comprises a method of growing a known species of truffle. The method comprises obtaining a spore-producing fruiting body of an ascomycetous fungus from soil, scraping the inside of the spore-producing fruiting body of the ascomycetous fungus to collect a fruiting body sample, placing the fruiting body sample on a first surface comprising a nutrient substrate, wherein the nutrient substrate comprises: a simple sugar, a botanical isolate, and agar, incubating the fruiting body sample on the nutrient substrate with an antimicrobial volatile mixture until mycelium formation, wherein the presence of mycelium indicates new fungal growth, transferring the new fungal growth into second surface comprising the nutrient substrate and a sterile medium selected from the group consisting of: nut or a portion thereof and a grain or a portion thereof to obtain an inoculant, combining sterile water with the inoculant at a preferred volume ratio 1 part inoculant to 4 parts water to produce a suspension, mixing the suspension with a soil mixture to produce a fungal soil mixture, applying the fungal soil mixture to a plant root or a portion thereof. In some aspects, the fungal soil mixture is air dried and stored at 3° C. In other aspects the fungal soil mixture is stored at −20° C., and at −80° C. The method may further comprise mixing the fungal soil mixture with the soil in the area where roots of host trees are growing, so as to inoculate with the pure culture of the ascomycetous fungus. In an additional embodiment, a truffle-growing composition is disclosed herein. The composition comprises a grain and mycelium from a truffle species. In some aspects of the disclosure, the truffle species contains at least one of: SEQ ID NO: 1, SEQ ID NO: 2, SEQ ID NO: 3, SEQ ID NO: 4, or SEQ ID NO: 5 and the grain is infested with the truffle species.

Another embodiment disclosed herein comprises a method for storing a pure culture of ascomycetous fungus. In some aspects, the method comprises providing sterile water, adding the pure culture of ascomycetous fungus to the sterile water to produce an inoculated solution, and storing the inoculated solution in a controlled temperature condition of 1-5° C. In another embodiment, a method for storing a pure culture of ascomycetous fungus comprises providing sterile medium selected from the group consisting of: a nut or a portion thereof and a grain or a portion thereof, inoculating the sterile medium with the pure culture of ascomycetous fungus to produce an infested seed population of ascomycetous fungus, and storing the infested seed population of ascomycetous fungus in a controlled temperature condition. In some aspects of the disclosure, the controlled temperature condition is −80° C. to −20° C. In some other aspects of the disclosure, the controlled temperature condition is 20° C. to 25° C., the method further comprises drying the seed population of ascomycetous fungus.

In still yet another embodiment, a method of making a truffle-flavored food product is herein disclosed. The method comprises incubating a pure culture of ascomycetous fungus with fruit, nut, grain, or a portion thereof for at least two weeks to produce an inoculated botanical sample and processing the inoculated botanical sample into a food product. In one aspect of the embodiment, the processing step of the method comprises at least one of: drying the product, grinding the inoculated botanical sample into a powder and creating a wet mash using the inoculated botanical sample and/or using the wet product in combination with some other product such as honey or maple syrup. In another aspect of the present disclosure, the powder or mash is mixed with a food product. In some non-limiting examples of food products, the powder or mash is used to create salts, oils, dressings, spreads, and drinks. The cultured truffle fungi can provide useful new food products and flavors when in a cultivated state.

Volatile Organic Compounds Mixture

In some embodiments of the present disclosure, the antimicrobial volatile mixture is derived from the volatile organic compounds produced by a *Muscodor* spp. organism.

About 20 years ago a novel but related ascomycete (*M. albus*) was isolated whose volatiles (VOCs) were lethal as well as inhibitory to many other microbes. This fungus was making volatile antibiotics, and some compounds were identical or related to those of the truffle fungi. Thus, the concept applied in this disclosure is that it is understood that a fungus species exists that does not kill itself nor its related ascomycetous (VOC-producing) fungal species could possibly kill or severely inhibit contaminating microbes that inhabit the truffle. It seemed likely that one could develop a technique that would readily allow for the virtual decontamination of the truffle without killing the fungus that made it and eventually allow for it to grow out on its base medium. Subsequently, another *Muscodor* sp. was isolated that made fewer VOCs and was just as active as *M. albus*. Thus, the selection technique for the truffle fungi is based on the VOCs of the new *Muscodor*, named *Muscodor crispans*. A further explanation of this procedure is given below.

The background information on the unique approach is based on the discovery of a novel endophytic fungus, *Muscodor albus*, and its related species. It has been learned that each of these species produces one or more biologically active volatile organic compounds that various targets, from insects to microbial organisms. Artificially prepared mixtures of these fungal-produced compounds all have the ability to mimic the biological effects of the fungus itself. This organism is one of the most effective biological weapons that has ever been found.

The *Muscodor* genus has 22 type species recognized as of 2023, and several isolates reported from the different geographic locations across the globe which are being continuously exploited for the development of numerous industrial applications. Some areas of industrial application include the agriculture sector followed by health, environment, and food. Members of *Muscodor* genus are some of the best studied fungi with respect to their gas chemistry (VOCs) which possess tremendous direct and indirect applications. All isolates have been found as endophytes and, for the most part, each possesses antimicrobial properties in the VOC stage using a well-established bioassay system. Furthermore, the chemistry of the VOC mixture is unique with respect to every individual *Muscodor* species that has been described.

*Muscodor albus*, the first isolate of *Muscodor*, released up to 37 different VOCs. An artificial mixture of at least 18 of these VOCs was prepared by organic synthesis, as well as product purchase and ultimately made into a mixture that closely mimicked the bioactivity of the fungus itself. The mixture had broad spectrum activity against a wide range of fungi but commonly *Trichoderma* spp. were relatively unaffected. Therefore, concerted efforts were made to find other species of this fungus having fewer VOCs but still having strong antimicrobial activities. The original fungus was used as a selection tool for these purposes. To this end, a novel *Muscodor* species appeared from a wild pineapple plant recovered from the reaches of the upper Amazon River Basin in Bolivia. The fungus was named *Muscodor crispans* and it was shown to produce only 17 VOCs and at least 5 of them were deemed as either non-essential to bioactivity or having questionable human and or environmental safety risks including such molecules as ethanol, ethyl acetate, formamide, N-(1-methylpropyl)-, cyclohexane, 1,2-dimethyl-3,5-bis(1-methylethenyl), and hexane, 2,3-dimethyl-D. Subsequently an artificial mixture of the remaining 12 compounds was made and tested and shown to be extremely active against a wide range of plant and human pathogenic fungi and bacteria. This mixture of *Muscodor crispans* VOCs was given the name of B-23 after the original designation of the place and the plant number given to the wild pineapple plant. Thus, this is how the B-23 mixture was discovered and now being applied as a key ingredient to isolate various *Tuber* spp. fungi (Table 3). The method was successfully applied to the isolation of truffle fungi belonging to the *Imaia* spp.

Thus, in some aspects, the antimicrobial volatile mixture comprises at least one of: propanoic acid, 2-methyl-, methyl ester; ethanol; acetic acid, 2-methylpropyl ester; propanoic acid, 2-methyl-, 2-methylpropyl ester; 1-propanol, 2-methyl-; 2-butenal, 2-methyl-, (e)-; 1-butanol, 3-methyl-, acetate; propanoic acid, 2-methyl-, 2-methylbutyl ester; 1-butanol, 3-methyl-; propanoic acid, 2-methyl-, or isobutyric acid; and acetic acid, 2-phenylethyl ester.

Truffle Species

The species of truffle to which the disclosed methods may be applied includes a *Tuber* spp. and *Iamai* spp. For example, the disclosed method grows a species of ascomycetous fungus selected from the group consisting of: *Tuber melanosporum, Tuber magnatum, Tuber aestivum, Tuber uncinatum, Tuber borchii, Imaia* spp., *Tuber macrosporum, Tuber gibbosum, Tuber oregonense*, and *Tuber lyonii* syn. *Texense*.

Figure 3A:
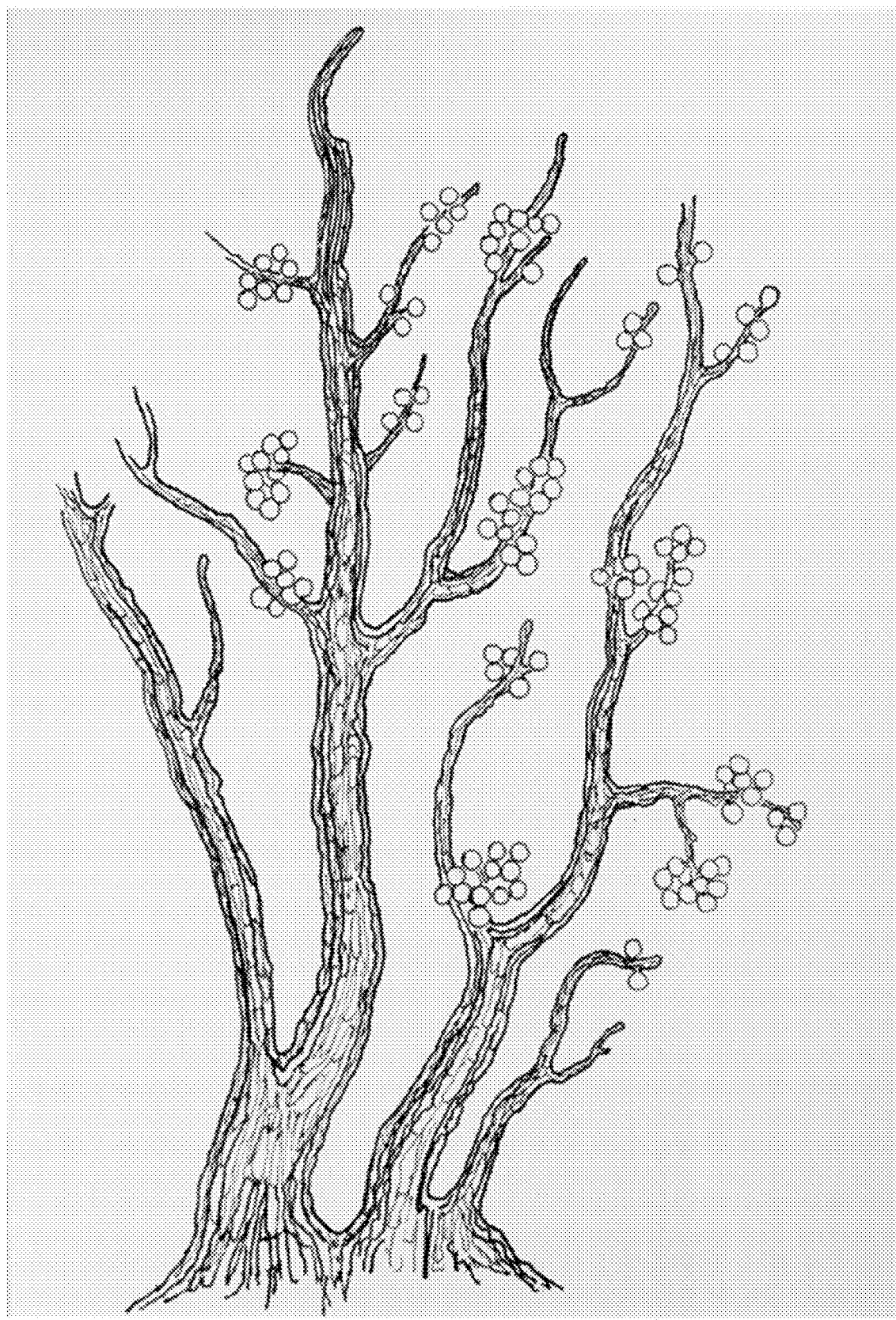
FIGS. 3A-3C are images illustrating the microscopic structure of the black truffle fungus.
Figure 3B:
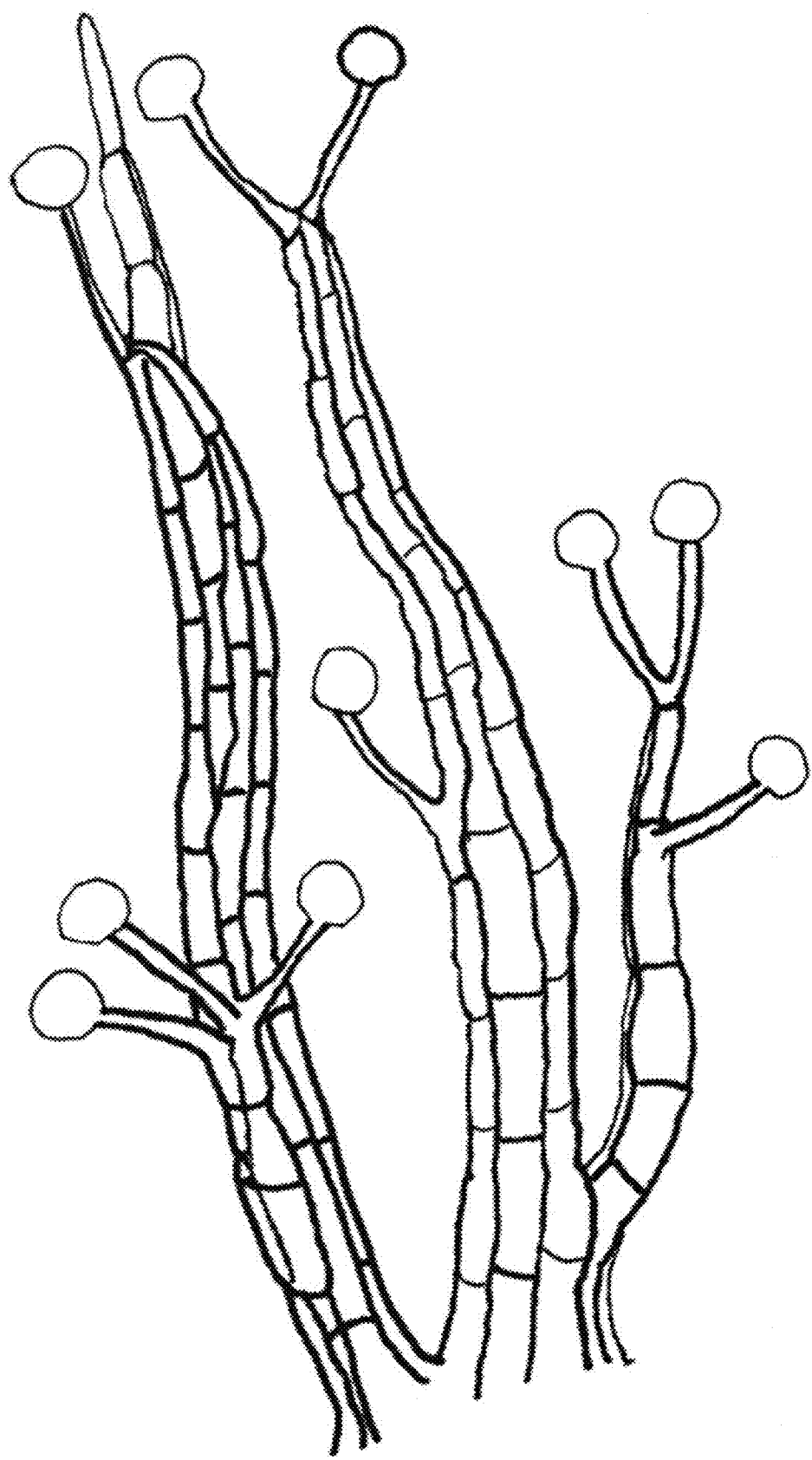
Figure 3C:
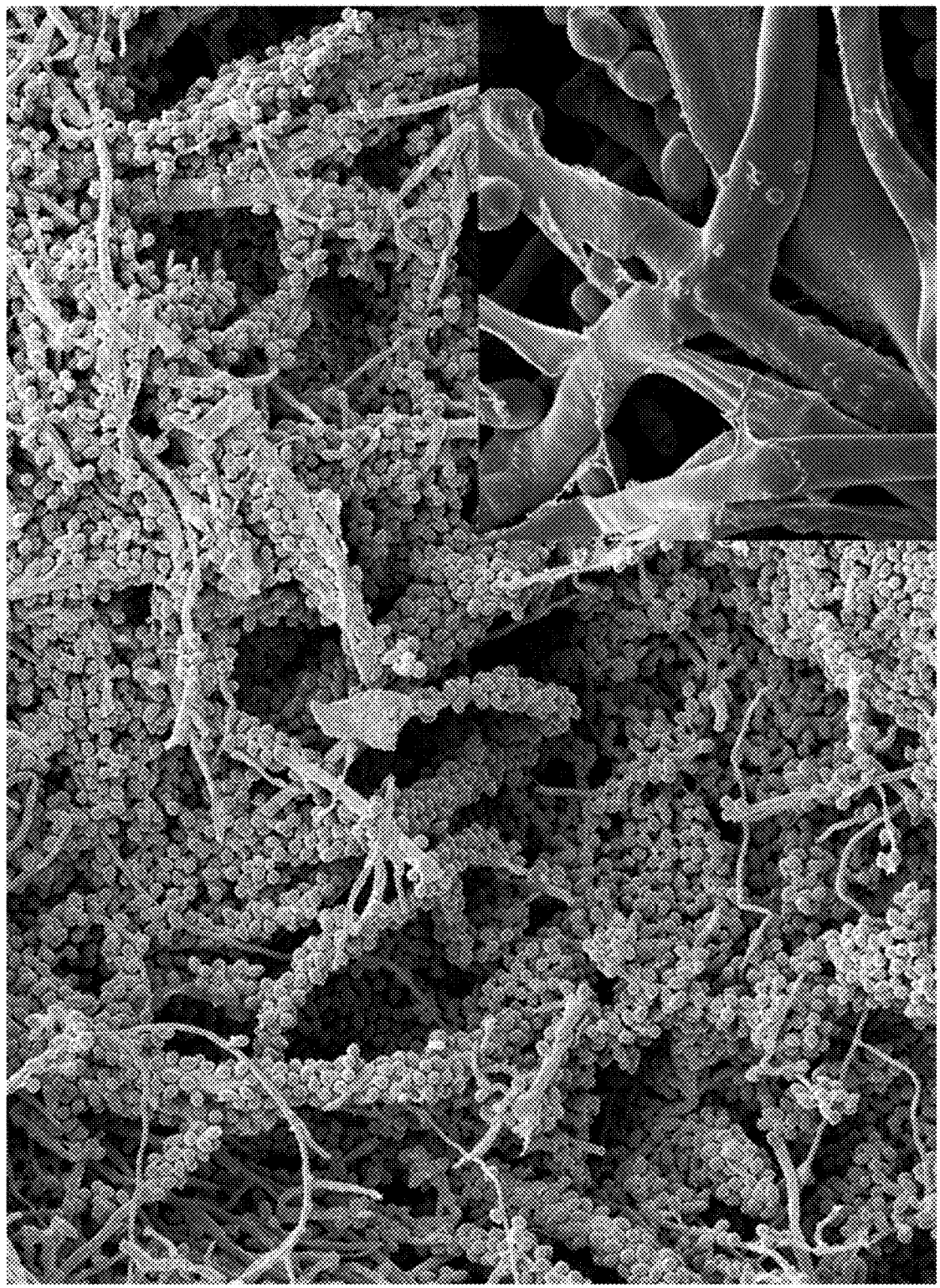
Figure 4:
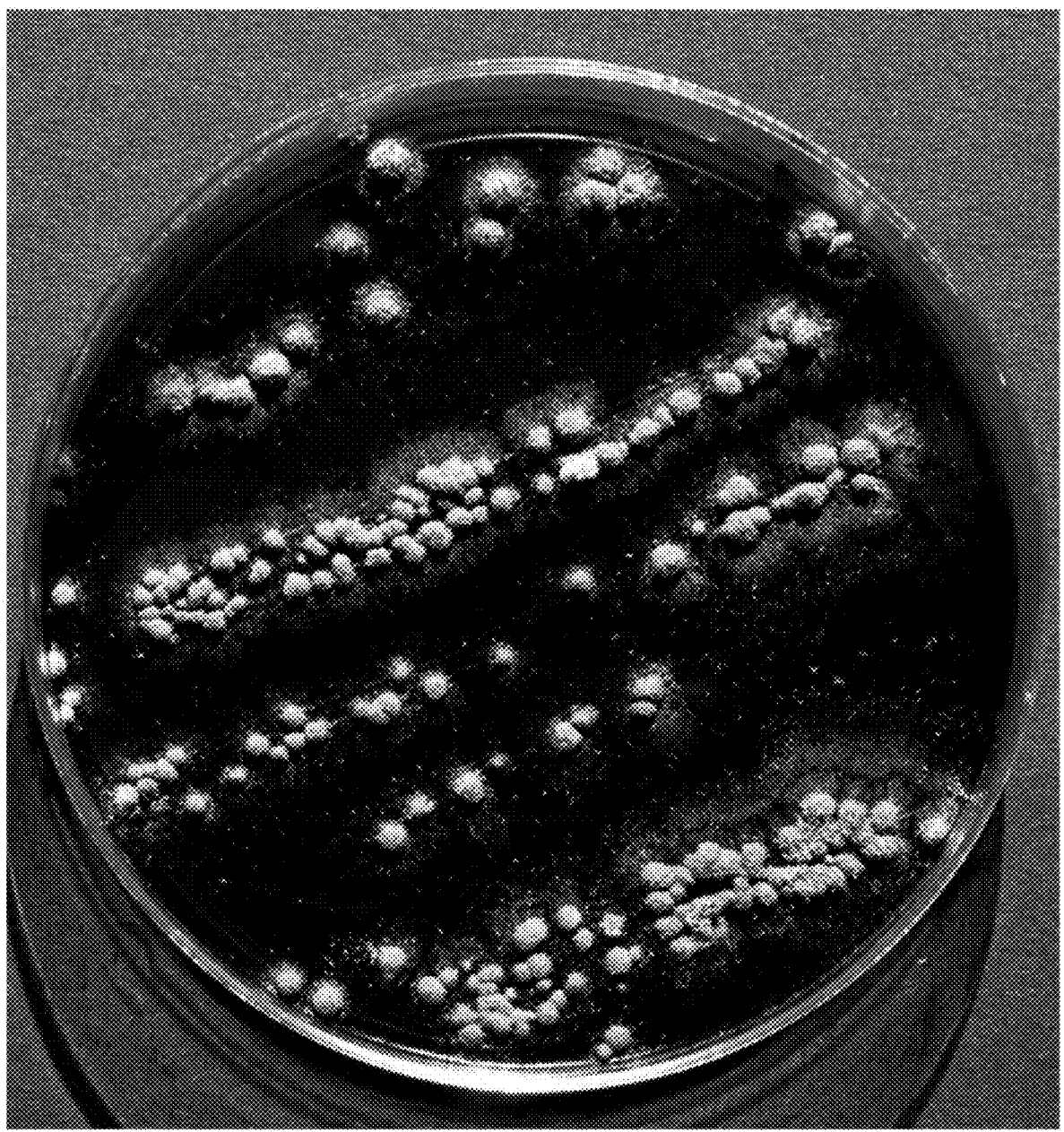
FIG. 4 is an image representation of the production of mini-truffles on PDA by the isolated culture of *T. melanosporum* that had been stored in honey for 6 days and then a small portion of the honey struck 5 times on a fresh plate of PDA and incubated for 10 months at 22° C. The dissected truffles had the same structures as a mature large field harvested truffle.

Briefly, some of the characteristics of isolated *Tuber melanosporum* or the black truffle are:

1. Relatively slow growth on PDA medium of 1 mm per day.
2. Production of slightly yellowish hyphae that become heavily interwoven.
3. Immediate production of fused hyphae into synnemata (fruiting structures).
4. Abundant production of conidiospores (conidia) on synnemata that are about 2.5μ in diameter (FIGS. 3, 4). Initially the spores are produced on the termini of branched conidiophores. Then on older synnemata they bud from the entire length of that structure (FIGS. 3,4).
5. Initial colony color is yellowish white eventually tuning gray then to black.
6. Older colonies turn grayish as a result of numerous synnemta and conidiophores and conidia (FIG. 5).
7. Definite truffle odor developing on the colonies. This odor is the result of the production of volatile organic compounds (VOCs) by the fungus. GC/MS analyses have been published for the black truffle as well as many of the other truffle fungi. The compounds identified by the standard SPME fiber analyses have revealed the presence of sulfur compounds, organic alcohols, acids, esters, aldehydes, ketones, as well as aromatic compounds, furans, terpenoids and others. It is to be remembered that all of the analyses published thus far in the literature were done on the intact truffle material and not on pure fungal cultures and that all truffles are made up of a huge complex mixture of microorganisms including bacteria, other fungal species, streptomycetes and even an occasional insect, not to mention plant tissue material on which the truffle forms. Thus, one would expect that a GC/MS analysis of a pure truffle culture would not be identical to that of the respective truffle type that it may produce since fungal products would and could be easily modified by the other microbes in the truffle tissues. This would yield a mixture of mostly bacterial and other fungal derived products. Nevertheless, GC/MS analyses of the VOCs of the black truffle culture did yield the following compounds that were common to published analyses of the black truffle itself including acetic acid, ethyl benzene, nonanal, decanal, ethyl benzene, 1,24 trimethyl benzene, and benzaldehyde. Most importantly was the detection of 3-thiophencarboxylic acid methyl ester. Thiophenes are known products of the truffle fungi. These products were found in samples obtained from 4- to 5-week-old cultures of the fungus having been grown on white rice as described below. Gases were sampled with the SPME fiber as well as solubilized gaseous compounds analyzed with the C8 solid phase extraction cartridge. The GC/MS data are supportive of the claim that the black truffle fungus has been successfully isolated. Obviously not all of the volatile compounds published for the black truffle were recovered here since the truffle represents a microbiome of many microbes and other organisms and they undoubtedly contribute to the complexity of the VOC composition, independently of the *Tuber* spp.

8. Eventual formation of mini-truffles on PDA plates. The fungus had been grown on sterile pecan fruits for 6 weeks and then placed in honey for 1 week. It was then struck on PDA and grown for a year on the plate where it produced mini-truffles (FIG. 4). Also, when a culture is transferred from PDA to the pecan agar, mini-truffle formation begins in about 6 weeks. This is, to our knowledge, the first report of such a discovery. It has major implications as another commercial product—that is artificially derived truffles.

9. The ITS sequence of the *T. melanosporum* is provided in SEQ ID NO: 1. It shares 99.8% identity with Cosmospora sp. but in no way is it identical to this fungus. Interestingly, in the literature, virtually all of the ITS sequences reported for the truffle fungi had their DNA extracted from the truffle itself which is composed of plant, other fungal and bacterial contaminants (11). Thus, one cannot obtain a valid determination of the actual ITS sequence in this manner. Only a pure fungal culture as a DNA source can yield accurate ITS sequence information as per above.

Figure 5:
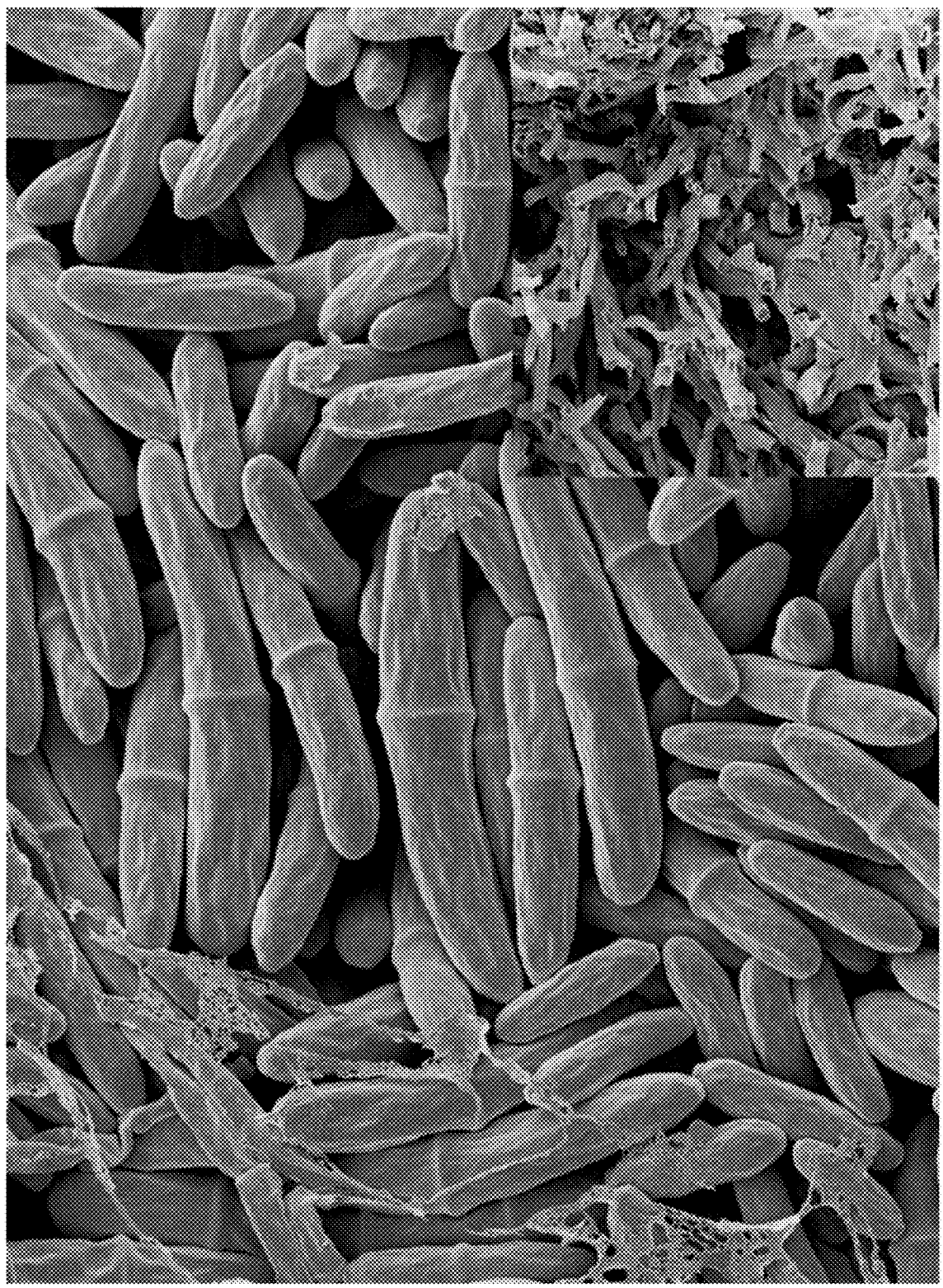
FIG. 5 is an image illustrating a scanning electron micrograph of conidiospores (conidia) of *T. magnatum* showing some as single celled (3.0 µm) and some larger ones as two celled-6.7 µm. The scarred conidiophore termini are shown in the insert.

Some of the characteristics of the white truffle (*Tuber magnatum*) are described below:

1. Relatively slow growth on PDA medium of 1.1 mm per day.
2. Production of slightly hyaline hyphae leading to whitish mycelia growth.
3. Immediate production of fused hyphae into synnemata (fruiting structures).
4. Abundant production of conidiospores (conidia) on conidiophores and multiple conidiophores (synnemata) that are dimorphous, some in the range of about 3.0 µm in length and other that are two celled and longer at about 6.7 µm (FIG. 5). Initially, the spores are produced on the termini of branched conidiophores and during the fixation processes the conidia break off from the conidiophores and leave scarred ends of these structures (FIG. 5 insert).
5. Initial colony color is white eventually with portions tuning tan to brownish.
6. Older colonies turn dark brown.
7. Definite truffle odor developing on the colonies.
8. Eventual formation of mini-truffles pecan agar plates at 1-2 weeks.
9. The ITS sequence of *T. magnatum* is provided in SEQ ID NO: 2. It is not identical to any of the other truffle species.

Figure 6:
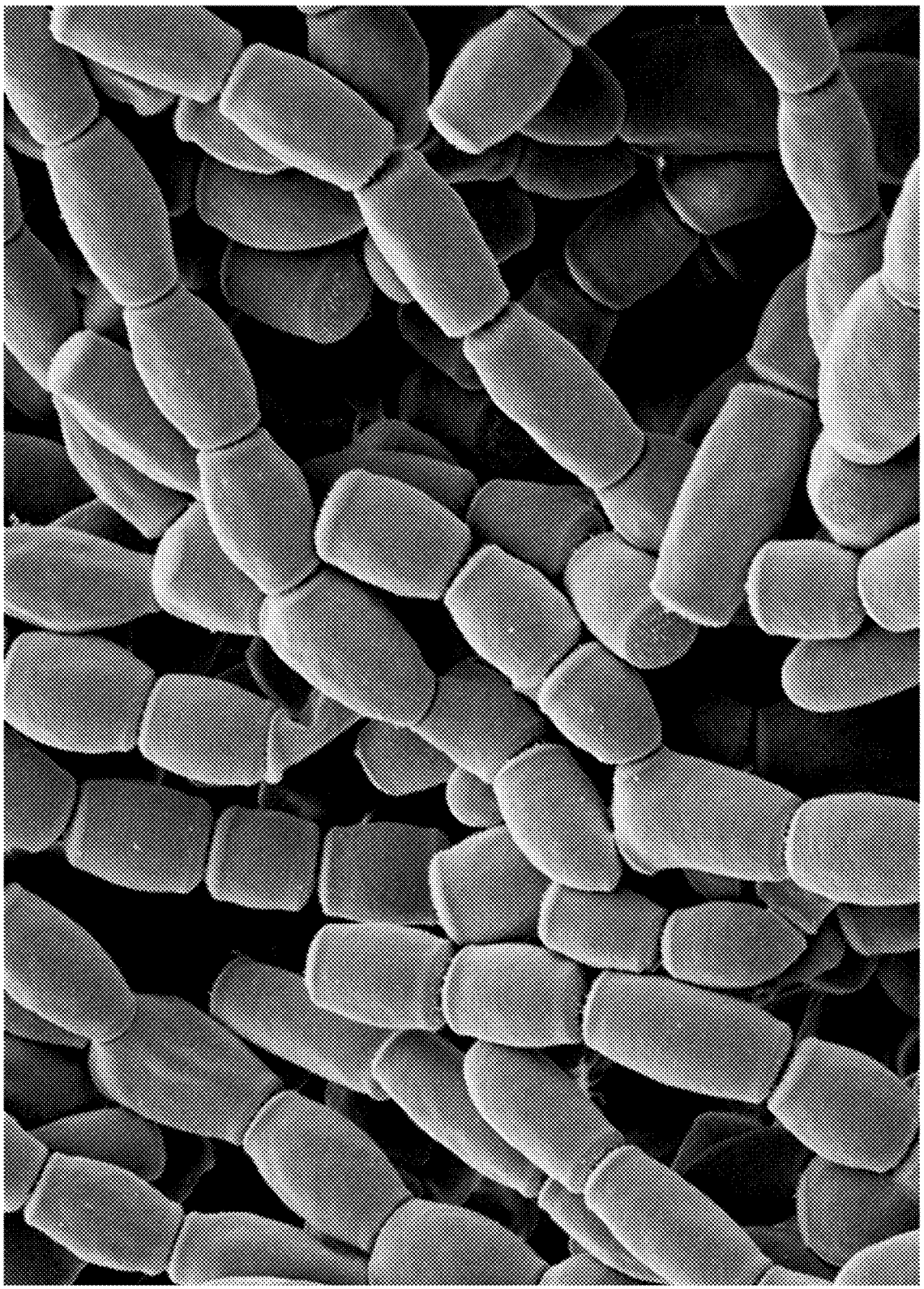
FIG. 6 is an image illustrating the arthrospores of *Tuber aestivum* (the summer truffle) showing the spores at a size of 3.5 µm in width and 5.2 µm in length as done by scanning electron microscopy.

Additionally, some of the characteristics of the summer truffle (*Tuber aestivum*) are described below:

1. Relatively rapid growth on PDA medium of 2.8 mm per day.
2. Production of hyaline hyphae leading to a white mycelium that forms interwoven rope like strands.
3. Production of conidiophores and then synnemata and many arthrospores (conidia). The spores are truncated, and barrel shaped with an average length of 5.2 µm and width of 3.5 µm (FIG. 6).
4. Older colonies stay whitish.
5. An initial fruit like odor developing in the culture plates.
6. Mini-truffles production in 2-3 weeks on the pecan agar.
7. The ITS sequence of *T. aestivum* is provided in SEQ ID NO: 3. It shows 98% sequence identity to *Geotrichum* which also makes arthrospores, but it is not a *Geotrichum* by all other indications.

Figure 8:
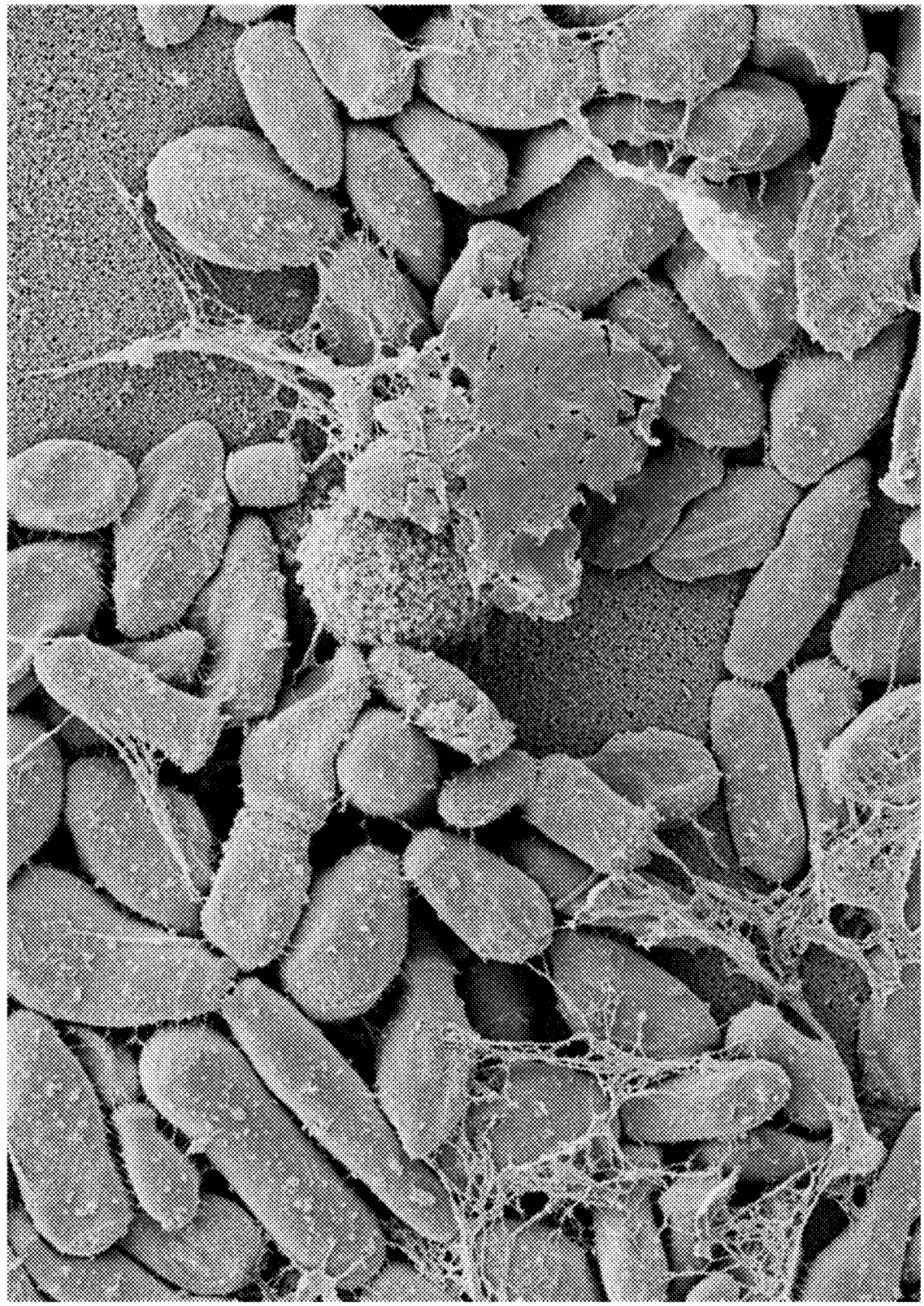
FIG. 8 is an image illustrating a scanning electron micrograph of the spores and hyphae of *Tuber uncinatum*. The spores shown vary widely in shape and size averaging 9.2 µm in length and 3.6 µm in diameter. Some of the matrix material of the mini-truffle pellicle is also shown.

Characteristics of the burgundy truffle (*Tuber uncinatum*) are shown below:

1. Relatively slow growing at 1.0 mm per day.
2. Production of hyaline hyphae eventually growing into a white mycelium that forms interwoven rope like strands.
3. Production of synnemata with abundant conidia born on conidiophores. The conidia are oddly shaped but do average 3.6×9.2 µm in size (FIG. 8).
4. After several weeks on PDA the culture medium begins to turn a burgundy color which supports the name of this interesting truffle.
5. At 4-5 weeks on pecan agar the fungus begins to make mini truffles that are whitish and small and having an erumpent surface just as the mature naturally harvested older truffles—i.e., 0.3 mm. Scanning electron micrographs show the formation of a nice pellicle layer over the mini truffle surface.
6. The cultures of this fungus commonly form a greasy appearance because of the huge number of conidia that are formed. The mycelium remains whitish over many months.
7. The ITS sequence of *T. uncinatum* is provided in SEQ ID NO: 4. It is not related to any of the other truffle fungi.

Figure 7:
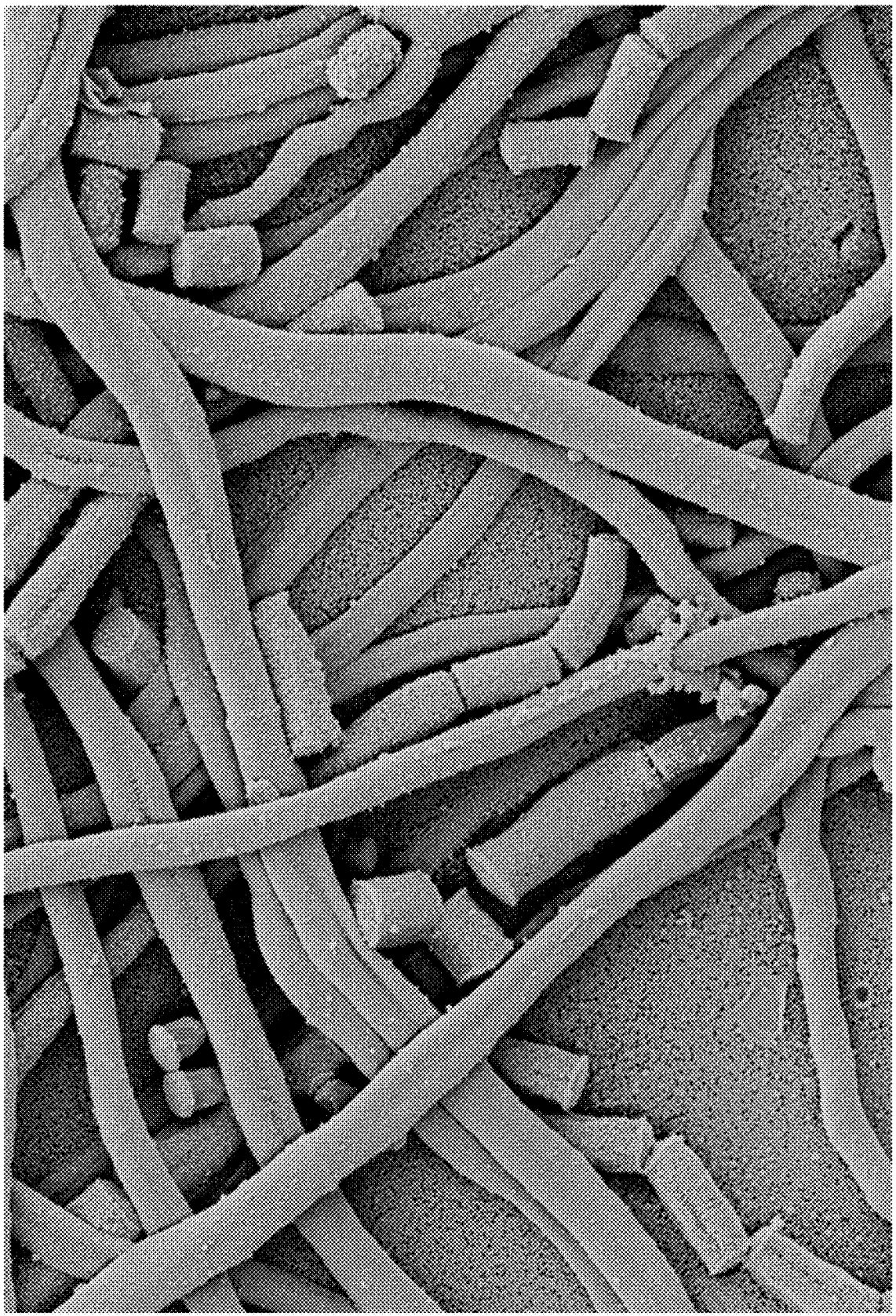
FIG. 7 is an image illustrating the hyphae and conidia of *Tuber borchii* as seen by scanning electron microscopy. The spores are averaging 4 µm in width and 5.6 µm in length with a few much longer.

Some of the characteristics of the whitish truffle fungus (*Tuber borchii*) are described below:

1. Relatively rapid growth on PDA medium of 3.0 mm per day.
2. Production of hyaline hyphae eventually growing into a white mycelium that forms interwoven rope like strands.
3. Production of conidiophores with conidia on termini of branches and then synnemata and many arthrospores (conidia). The spores are truncate and barrel shaped with an average length of 5.6p and width of 4.0µ (FIG. 7).
4. Older colonies stay whitish
5. An initial fruit like odor developing in the culture plates.
6. Mini-truffle production in 2-3 weeks on pecan agar.
7. The ITS sequence of *T. borchii* is provided in SEQ ID NO: 5. The sequence is very closely related to the sequence of *T. aestivum* but not to the other truffle fungi as per *T. melanosporum* (above).

Characteristics of the North American truffle fungus (*Imaia* sp.) are described below:

*Imaia* is a fungal genus in the family Morchellaceae found in Japan, and in the Appalachian Mountains of the US. A monotypic genus, *Imaia* was circumscribed in 2008 by James Martin Trappe and Gibor M. Kovácsto to contain the truffle-like species formerly known as *Terfezia gigantea* when molecular analysis demonstrated that its DNA sequences were markedly different from those of *Terfezia*.

The fruit bodies of *Imaia gigantea* are spherical to roughly elliptical to irregular in shape, brown, and usually develop cracks in age. The interior gleba comprises brown pockets of asci separated by white veins. The spores are spherical or nearly so, up to 70 μm long, and enclosed by a thick epispore.

After isolation and examination, it showed the following characteristics:

1. Hyaline hyphae growing on PDA at a rate of 2.5 mm per day at 22° C.
2. Producing a totally whitish mycelium not developing any pigmentation over several months held on PDA.
3. It produced whitish mini—truffles 3-5 mm in diameter on pecan agar after two weeks of incubation at 22° C.
4. It produced a mixture of a wonderfully aromatic mixture of volatile organic compounds after a week having been grown on PDA.
5. It produced an abundance of synnemata on PDA and the conidiospores (arthrospores) associated with the synnemata resembled (in size and shape) those of both *T. aestivum* and *T. borchii* (FIG. 6 and FIG. 7).
6. The fungus was fermented on Thompson seedless grapes as well as ground pecans for two weeks at 22° C. The decanted filtered grape juice was given a ranking of 8.5 whilst the unfermented juice was ranked at 6.0 (see Table 7 below). Also, the fungus product from pecans was dried and ground. It produced a powder with a nice truffle taste having a pecan tasting background (see Table 5 below).
7. This truffle fungal isolate can be saved by growing it on sterilized white rice grains for several weeks and then putting them in cryovials and placing them at −80° C. or placing the conidiospores in vials with sterile water and storing at 2-3° C. (see section on storage below).

Table 1 provides brief description of commercial truffle species. Table 2 lists ITS sequences for pure culture of truffle. Each of the truffle fungi described in Tables 1 and 2 were originally obtained, as freshly harvested truffles, from their natural geographic sources and then used as a biological source of the pure cultures once these organisms were successfully isolated.

TABLE 1

| Brief Description of Truffle Species | | |
|---|---|---|
| Common Name | Species | Brief Description |
| Black Truffle | *Tuber melanosporum* | The black truffle or black Périgord truffle, the second-most commercially valuable species, is named after the Périgord region in France. Black truffles associate with oaks, hazelnut, cherry, and other deciduous trees and are harvested in late autumn and winter. |
| White Truffle | *Tuber magnatum* | This high-value white truffle (tartufo bianco d'Alba in Italian) is found mainly in the Langhe and Montferrat areas of the Piedmont region in northern Italy, and most famously, in the countryside around the cities of Alba and Asti. A large percentage of Italy's white truffles also come from Molise. |
| Summer Truffle | *Tuber aestivum* | The black summer truffle is found across Europe and is prized for its culinary value. |
| Burgundy Truffle | *Tuber uncinatum* | Burgundy truffles (designated Tuber uncinatum) are harvested in autumn until December and have aromatic flesh of a darker color. These truffled associate with various trees and shrubs. |
| Whitish Truffle | *Tuber borchii* | The "whitish truffle" is a similar species native to Tuscany, Abruzzo, Romagna, Umbria, the Marche, and Molise. It is reportedly not as aromatic as those from Piedmont, although those from Città di Castello are said to come quite close. |
| An Appalachian truffle | *Imaia* spp. | This species is found in very limited areas in the Appalachian Mountains of Eastern USA. |
| "garlic truffle" | *Tuber macrosporum* | Less common truffle. |
| Oregon black truffle; Oregon spring white truffle | *Tuber gibbosum*; *Tuber oregonense* | Notable U.S. Pacific Northwest species of truffles, among several species of truffle harvested both recreationally and commercially. |
| Pecan truffle | *Tuber lyonii* syn. *Texense* | Found in the Southern United States, usually associated with pecan trees. Chefs who have experimented with them agree "they are very good and have potential as a food commodity." |

TABLE 2

ITS Sequences for Isolated Truffle Fungi

| SEQ ID NO | Truffle Species | ITS Sequence |
| --- | --- | --- |
| SEQ ID NO: 1 | T. melanosporum | CCTGTGACATACCTATTGTTGCTTCGGCGGGATCGCCC CGGCGCCCTCGGGCCCGGACCCAGGCGCCCGCCGGA GGACCCAAACTCTTGTCTTCATGAGAATCTTCTGAGT AACACAAGCAAATAAATTAAAACTTTCAACAACGGAT CTCTTGGTTCTGGCATCGATGAAGAACGCAGCGAAAT GCGATAAGTAATGTGAATTGCAGAATTCCGTGAATCA TCGAATCTTTGAACGCACATTGCGCCCGCCAGTATTCT GGCGGGCATGCCTGTTCGAGCGTCATTTCAACCCTCA AGCCCCCGGGCTTGGTGTTGGGGATCGGCCGCCCTCC GGCGCGCCGGCCCCGAAATCTAGTGGCGGTCTCGCTG TAGCCTCCTCTGCGTAGTAACACACCTCGCACCGGAA CGCAGCCTGGCCACGCCGTTAAACCCCCCACTTCTGA AGGTTGACCTCGGATCAGGTAGGAATACCCGCTGAAC TTAAGCATATCAATAAGCGGAGGAA |
| SEQ ID NO: 2 | T. magnatum | CCCTGTGACATACCATATTGTTGCCTCGGCGGTGCCTG TTTCGGCAGCCCGCCAGAGGACCCAAACCCTAGATTA CATTAAAGCATTTTCTGAGTCAATGATTAAATCAATC AAAACTTTCAACAACGGATCTCTTGGTTCTGGCATCG ATGAAGAACGCAGCGAAATGCGATAAGTAATGTGAA TTGCAGAATTCAGTGAATCATCGAATCTTTGAACGCA CATTGCGCCCGCCAGTATTCTGGCGGGCATGCCTGTC CGAGCGTCATTTCAACCCTCAAGCCCCCGGGCTTGGT GTTGGAGATCGGCGAGCCCCCGGGGCGCGCCGTCTC CCAAATATAGTGGCGGTCCCGCTGTAGCTTCCTCTGC GTAGTAGCACACCTCGCACTGGGAAACAGCGTGGCCA CGCCGTAAAACCCCCCACTTCTGAAAGGTTGACCTCG GATCAGGTAGGAATACCCGCTGAACTTAAGCATATCA ATAAGCGGAGGAA |
| SEQ ID NO: 3 | T. aestivum | GTGANTTACACNGCAACAATAATTTTATANTCAAANA CNNAAAATAATCAAAACTTTTAACAATGGATCTCTTG GTTCTCGTATCGATGAAGAACGCAGCGAAACGCGATA TTTCTTGTGAATTGCAGAAGTGAATCATCAGTTTTTGA ACGCACATTGCACTTTGGGGTATCCCCCAAAGTATAC TTGTTTGAGCGTTGTTTCTCTCTTGGAATTGCATTGCT TTTCTAAAATTTCGAATCAAATTCGTTTGAAAAACAA CACTATTCAACCTCAGATCAAGTAGGATTACCCGCTG AACTTAAGCATATCAANNNGCGGAGG |
| SEQ ID NO: 4 | T. uncinatum | ACTATATCCATCTACACCTGTGAACCGTTTGATTGAAT CTTCTGATTCAATTTTACAAACATTGTGTAATGAACGT CATTAGATCATAACAAAAAAAAACTTTTAACAACGGA TCTCTTGGCTCTCGCATCGATGAAGAACGCAGCGAAA TGCGATAAGTAATGTGAATTGCAGAATTCAGTGAATC ATCGAATCTTTGAACGCAACTTGCGCTCTCTGGTATTC CGGAGAGCATGCCTGTTTGAGTGTCATGAAATCTCAA CCATTAGGGTTTCTTAATGGCTTGGATTTGGAGGTTGC CATTCTAAATGGCTCCTCTTAAAGGAGTTAGCAAGTT TTACTATTGCTATCTGGCGTAATAAGTTTCGCTGGAAT GGTATTGTGAAGCGTGCTTCTAATCGTCTTCGGACAA TTACTTTGACTCTGGCCTCAAATCAGGTAGGACTACC CGCTGAACTTAAGCATATCAATAAGCGGAGGAA |
| SEQ ID NO: 5 | Tuber borchii | TTGTGATTTACCACAGCAACAAAAATCATACAATCAA AACAAAAATAATTAAAACTTTTAACAATGGATCTCTT GGTTCTCGTATCGATGAAGAACGCAGCGAAACGCGAT ATTTCTTGTGAATTGCAGAAGTGAATCATCAGTTTTTG AACGCACATTGCACTTTGGGGTATCCCCCAAAGTATA CTTGTTTGAGCGTTGTTTCTCTCTTGGAATTGCTTTGCT CTTCTAAAATTTCGAATCAAATTCGTTTGAAAAACAA CACTATTCAACCTCAGATCAAGTAGGATTACCCGCTG AACTTAAGCATATC |

Basically stated, each of the many truffle fungi listed above are now available in pure culture. These truffle fungi can now be grown on a plethora of natural or artificial media which will make available an untold number of possible novel products each with a different set or combination of flavors. That is, since the fungus has been provided with different substrates on which to grow thus converting substances in the growth source to other flavor-like compounds and combinations thereof. Likewise, the isolation procedure will readily allow for the recovery of numerous local strains of the fungus which may prove useful in finding stand alone and unique natural foods. In this case, novel flavors can be created by actually growing the truffle fungus on grains, nuts, powders, floral parts or literally natural food source or mixtures of such products.

Figure 11:
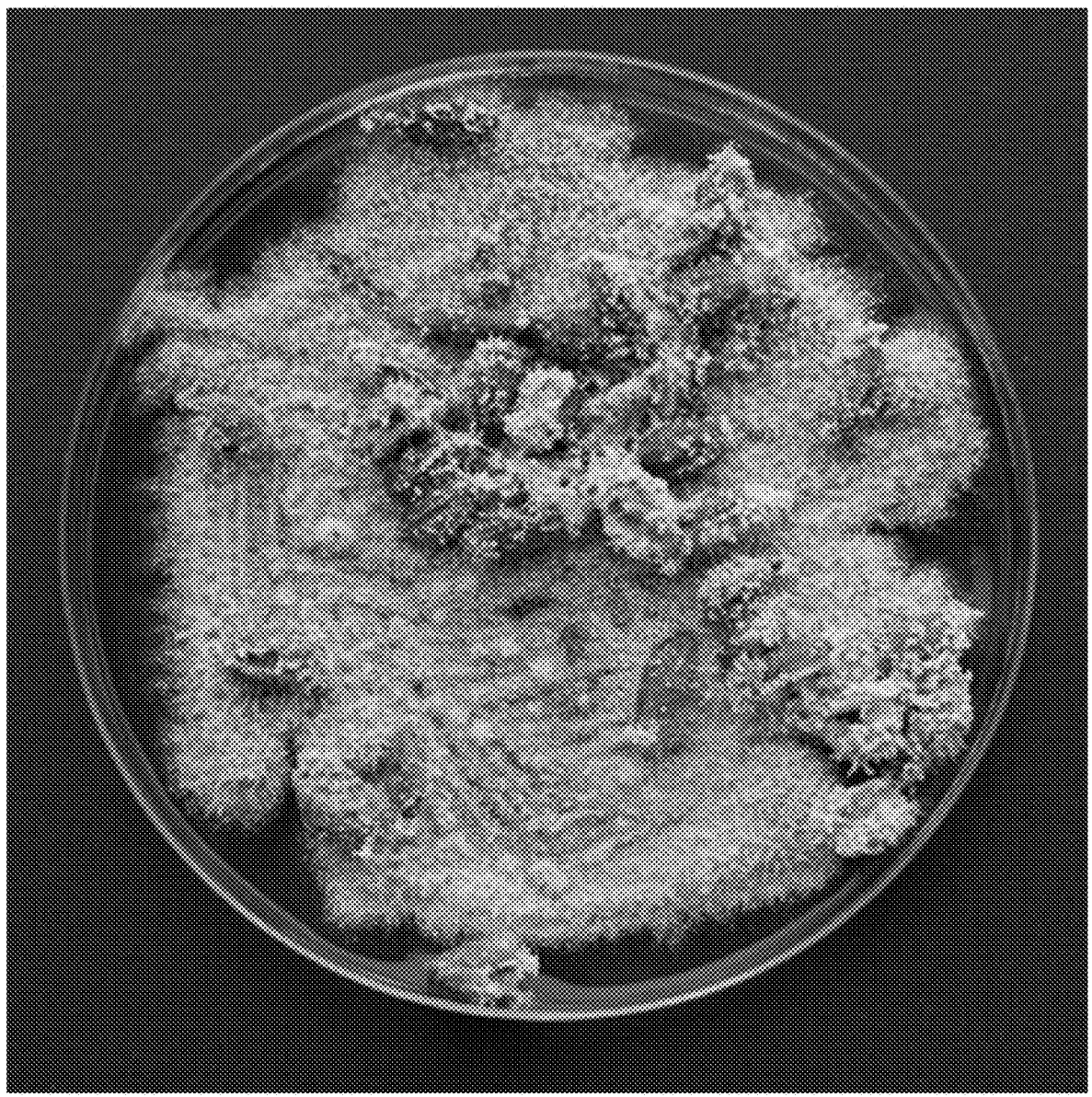
FIG. 11 is an image showing an older culture of the black truffle fungus (*T. melanosporum*). The gray coloration is the result of myriads of synnemata producing a plethora of conidiospores. The fungus is growing on sterilized barley seeds.
Figure 13:
FIG. 13 is an image showing one year old dried barley seeds infested with *T. melanosporum* placed in damp soil for 2 days already show the production of new mycelium, synnemata and spores (arrows).

Presently, trees are inoculated with the truffle fungi by dipping the roots into a puree of the truffle fungus that is desired. This is a costly, unsatisfying, and non-scientific proposition since the truffles themselves are not containing a myriad of infectious conidiospores and are contaminated with a plethora of other fungi and bacteria all of which portend of unexpectedly poor and undesirable outcomes. However, now with pure cultures of many truffle fungi can be easily grown on sterile grains such as de-hulled barley, rye, wheat or rice wherein there is an abundant production of infectious conidiospores (FIG. 11). These grains, after two—3 weeks of fungal growth can be dried under aseptic conditions at room temperature and stored under refrigeration (freezing or 40° F.) or at room temperature (22° F.) for up to a year with no significant decline in viability (FIG. 13). Subsequently, these infested grains can be used as inoculum for plant roots by placing them near to the roots of the desired plant species that will serve as the host.

EXAMPLES

The present disclosure is further illustrated by the following examples that should not be construed as limiting. The contents of all references, patents, and published patent applications cited throughout this application, as well as the Figures, are incorporated herein by reference in their entirety for all purposes.

Example 1. Isolation Procedures for Major Truffle Species for Domestication

Figure 2:
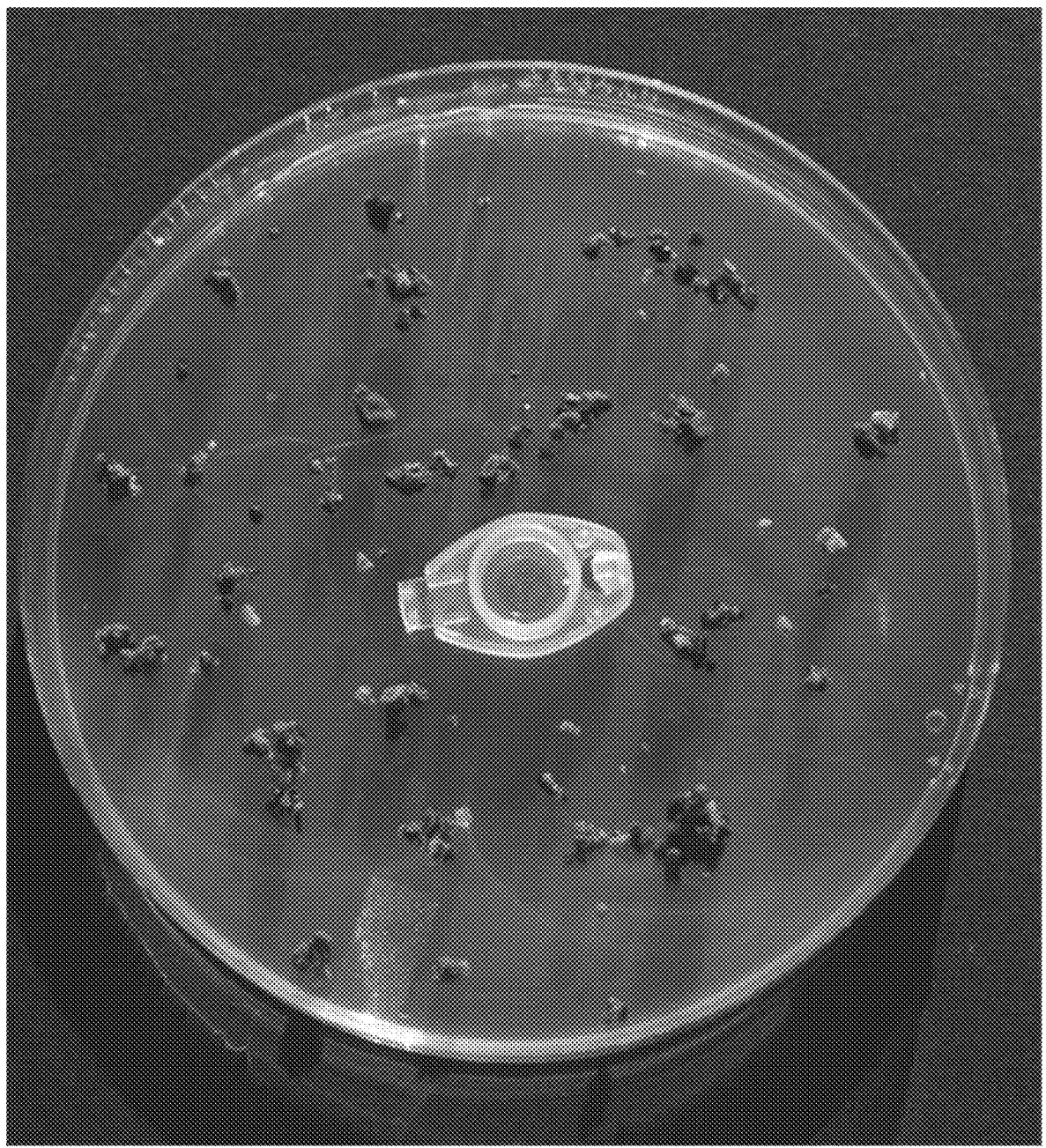
FIG. 2 is an image representation of the distribution of freshly cut pieces of the truffle over the potato dextrose agar (PDA) surface showing the placement of the plastic center well onto the plate that contains the B-23 mixture. The plates are then sealed with Parafilm® tape.

The isolation of an individual targeted truffle species was initiated by locating it fresh from a commercial intact truffle source. The truffles were cleaned, rinsed, dried and forwarded to our Montana address by rapid delivery services. The procedure described below is applied best to intact truffles. The truffles were stored, wrapped in paper toweling, and stored at refrigerator temperature. Each truffle was cut and then torn open. The freshly exposed surfaces were scraped into small, approximately 0.5-2 mm pieces directly onto a Petri plate containing potato dextrose agar (PDA) (FIGS. 1 & 2). A detached top cap lid from a small microcentrifuge vial was placed on the center of the plate. The lid then had 10 microliters of the B-23 solution added to it. The composition of B-23 is described in Table 3. The B-23 patented product mixture is available through Jeneil Biotech Co. Saukville, WI. The truffle pieces were liberally distributed around the plate (FIG. 2). The plates were incubated for 3-4 days at 22° C. and, at that point, it was noted that some microbial growth appeared well away from the center well but not immediately next to the center well. After 5 days of incubation, one could begin to carefully pick mycelial fragments of fungal colonies that appeared to be *Tuber* spp. Those fungal colonies having synnemata were especially targeted for transfer. The transfer of colonies was done with a sterile sharp knife tip. Also, the Petri plate lid was removed (degassed) and the cover returned to the plate. Over the course of several more days those particles next to the well were closely examined for fungal growth. Once growth occurred, the agar pieces containing fungal hyphal tips were carefully picked and transferred to new PDA Petri plates. Any remaining bacterial contaminants were removed by placing small amounts of powdered tetracycline HCL over the culture. Fungi suspected of being *Tuber* spp. were then examined for their ability to produce synnemata, asexual spores, pigments and the classic truffle odors. The entire process requires one skilled in the art of fungal biology and in particular truffle fungal biology to be able to correctly distinguish these fungi. The first *Tuber* sp. to be isolated in this manner was *Tuber melanosporum*. The isolates met all the culture and morphological characteristics of that particular fungus as described above.

TABLE 3

GC/MS analysis of the volatile compounds produced by *M. crispans*. Several minor peaks and the breakthrough peak were omitted from the total analysis since they represent only 1% of the total area. Compounds found in the control PDA plate are not included in this table.

| Retention Time Min. | Total Area | Possible Compound | MW Da |
|---|---|---|---|
| 2:05 | 1.39 | Acetaldehyde *+ | 44.03 |
| 3:40 | 6.23 | Ethyl Acetate *+ | 88.05 |
| 3:51 | 2.83 | 2-Butanone *+ | 72.06 |
| 4:08 | 30.56 | Propanoic acid, 2-methyl-, methyl ester * | 102.07 |
| 4:18 | 12.41 | Ethanol * | 46.04 |
| 5:29 | 2.29 | Acetic acid, 2-methylpropyl ester * | 116.08 |
| 6:39 | 1.09 | Propanoic acid, 2-methyl-, 2-methylpropyl ester * | 144.12 |
| 6:46 | 1.78 | 1-Propanol, 2-methyl- * | 74.07 |
| 6:52 | 1.51 | 2-Butenal, 2-methyl-, (E)- * | 84.06 |
| 7:12 | 4.79 | 1-Butanol, 3-methyl-, acetate * | 130.10 |
| 8:18 | 3.01 | Hexane, 2, 3-dimethyl-#+ | 114.14 |
| 8:21 | 4.78 | Propanoic acid, 2-methyl-, 2-methylbutyl ester * | 158.13 |
| 8:31 | 5.38 | 1-Butanol, 3-methyl- * | 88.09 |
| 13:37 | 351.18 | Propanoic acid, 2-methyl- * | 88.05 |
| 14:41 | 3.94 | Formamide, N-(1-methylpropyl)-+ | 101.08 |
| 16:44 | 1.31 | Acetic acid, 2-phenylethyl ester * | 164.08 |
| 20:44 | 7.20 | Cyclohexane, 1,2-dimethyl-3,5-bis(1-methylethenyl)-+ | 192.19 |

* Denotes that the indicted compound had the same retention time (RT) and mass spectrum (MS) as an authentic standard. Also indicates that the compound was used in the artificial mixture of VOCs. All other compounds in the list are matched to the most likely compound in the NIST data base, but the data have not been confirmed by use of an appropriate identical standard compound by either retention time or MS.
Denotes that the authentic standard did not have the same retention time as the compound indicated.
+Denotes not used in the B-23 formula mixture.

*Denotes that the indicted compound had the same retention time (RT) and mass spectrum (MS) as an authentic standard. Also indicates that the compound was used in the artificial mixture of VOCs. All other compounds in the list are matched to the most likely compound in the NIST data base, but the data have not been confirmed by use of an appropriate identical standard compound by either retention time or MS. #Denotes that the authentic standard did not have the same retention time as the compound indicated.+ Denotes not used in the B-23 formula mixture. The B-23 mixture is made by adding each of the components shown in this figure as a volume amount taken from the total area calculation in this table. Propanoic acid has been substituted for isobutyric acid at 13.37 min. because of the rancid nature of this acid.

To isolate a pure culturel *Imaia* spp., a shipment of about 1.5 kg of freshly harvested truffles were obtained from a grower in North Carolina. One of the truffles was rinsed with a spray of 70% ethanol and air dried. Then a sharp sterilized blade was inserted into the flesh of the truffle, and it was broken along the line of the inserted blade to reveal an untouched internal truffle surface. The sterile blade tip was also used to remove pieces of truffle flesh on to a Petri plate (PDA). At the center of the plate was placed a small plastic well containing 10 µl of the B-23 mixture and the plate was sealed with two wrappings of parafilm. The plate was set to incubate for 4 days at 22° C. At the end of that time only one fungal colony had grown out of the truffle fleshy pieces. The colony was labeled NC-1 and struck on other PDA plates and checked for cultural purity. The culture had the promising qualities of being another pure culture isolate of a truffle fungus. After further examination it showed the characteristics described above.

Materials and Methods

1. Mini-Truffles and Pecan Agar

This agar was made and tested because *T. melanosporum* was grown on ground pecans for 6 weeks, then placed in honey for 1 week to kill the fungus, and then spread on a PDA plate to determine if killing had occurred. Very unexpectedly, the fungus seemed to round up into little balls of mycelium within a week and then after 1 year the little balls appeared as mini-truffles, that is tightly knitted small round balls in the range of 2 mm in diameter—visible to the eye but smaller than normally expected from wild truffles. In comparison, on regular agar PDA the fungus only grew as flat mycelium and no mini-truffles have ever appeared. Thus, it seemed that the ingredients in the pecan were able to induce mini-truffle formation in this fungus. Therefore, a special pecan agar was concocted to be used as a substrate to learn if it alone would induce truffle formation in each of the putative truffle fungi. If this were the case, then this medium could serve as a test medium to ascertain if any putative fungus may be a truffle fungus and thus serve as an additional supportive information for the identity of the organism.

The ingredients of the pecan agar are below:

10 g finely ground pecans
2.5 g glucose
0.5 g peptone
1 g yeast extract
3 g agar Make up to 200 ml of water and autoclave for 20 min. Pour plates with 35 ml of fluid.

The plates are then inoculated with a pure culture of each of the truffle fungi.

The plates were incubated for 2-3 weeks at 22° C. and then photographed at that point in time when mini-truffles began to appear.

2. Scanning Electron Microscopy (SEM)

SEM was performed on the truffle isolates having been grown on the pecan agar (see below) for varying periods depending upon the given isolate. Agar pieces supporting fungal growth were placed in filter paper packets then placed in 2% glutaraldehyde in 0.1 M sodium cacodylate buffer (pH 7.2-7.4) with Triton X 100, a wetting agent, aspirated for 5 min and left overnight. The next day they were washed in six 15 min changes in water buffer 1:1, followed by a 15 min change in 10% ethanol, a 15 min change in 30% ethanol, a 15 min change in 50% ethanol, five 15 min changes in 70% ethanol, and were then left overnight or longer in 70% ethanol. They were then rinsed six times for 15 min in 95% and then three 15 min changes in 100% ethanol. The microbial material was critical point dried using a Tousimis Autosamdri® 931 GL critical point dryer, sputter coated with AuPd (80:20) using a Quorum Q 150T ES sputter coater, and images were recorded with a ThermoFisher Apreo C SEM. Hyphae were measured using Image J software (available online: http://rsb.info.nih.gov/ij/).

3. ITS—DNA Sequencing of the Truffle Fungi

DNA extraction—A quick DNA extraction method was used to acquire genomic DNA from the fungal isolates. Mycelium was picked up with the help of a sterile pipette tip and transferred to a 0.2 ml Eppendorf tube containing 15µ of Kawasaki lysis buffer (10 mM Tris HCl pH 8, 1 mM EDTA, 0.5% Tween 20, 10 µg/ml Proteinase K) and 15 µl of ultrapure water, followed by a 15 minutes incubation at 85° C. After the incubation time, tubes were centrifuged for 1 minute at 10000 rpm. DNA was extracted in replicates of two per fungal isolate.

PCR method—Fungal DNA was amplified using the rRNA gene primers ITSiF and ITS4R (9). PCR reactions (20 µl) was performed in 0.2 ml Eppendorf tube and contained 2 µml of template DNA, 10 µl of 2×PCR Hot Start Green Master Mix, and 500 nM of each primer. PCR thermocycler conditions consisted of an initial denaturation step of 95° C. for 5 minutes, followed by 35 amplification cycles of 95° C. for 30 s, 55° C. for 30 s, 72° C. for 60 s, and a final extension step of 72° C. for 10 min. All reactions were done in duplicate. Amplification was visualized in 1% agarose gel stained with GelRed® nucleic acid gel stain, at 10000×.

PCR products were purified and Sanger sequenced at Genewiz/Azenta in New Jersey. Sequencing results were blasted against the NCBI database. Ms. Erica Consoli of MSU performed these analyses.

4. Gas Chromatography/Mass Spectroscopy of *Tuber* Spp. Volatiles (VOCs)

A solid-phase micro-extraction syringe was used for trapping the fungal truffle volatiles (in the gas phase) that followed the procedure used to analyze the VOCs of *Muscodor albus*. The fiber material (Supelco) was 50/30 divinylbenzene/carburen on polydimethylsiloxane on a stable flex fiber. The syringe was placed through a small hole drilled in the side of the Petri plate and exposed to the vapor phase for 45 min. The syringe was then inserted into a gas chromatograph (Agilent 8890) equipped with a mass-selective detector. A 30 m×0.25 mm i.d. 5% phenyl methylpolysiloxane (HP-5 ms) Agilent J&W capillary column with a film thickness of 0.25 µm was used for the separation of the volatiles. The column was temperature programmed as follows: 25° C. for 2 min, then increased to 220° C. at 5° C. min$^{-1}$. The carrier gas was helium (ultra high purity (UHP); local distributor) and the initial column head pressure was 50 kPa. The helium pressure was ramped with the temperature ramp of the oven to maintain a constant carrier gas flow velocity during the course of the separation. Prior to trapping the volatiles, the fiber was conditioned at 240° C. for 20 min under a flow of helium gas. A 30 s injection time was used to introduce the sample fiber into the gas chromatograph. The chromatograph was interfaced to an Agilent 7000D triple quadrupole mass spectrometer operating at a mass resolution of 1500. The mass spectrum was scanned at a rate of 0.50 s per mass decade over a mass range of 35-360 Da. Data acquisition and data processing were performed on the Agilent Mass Hunter software package. Initial identification of the unknowns produced by the fungus was made by library comparison using the NIST database.

Analysis of compounds with a lower concentration in the vapor phase was achieved by growing the fungus on a rice/water slurry. The water extract from this mixture (25 mL) was filtered through Whatman number 2 paper then applying the solution to a C8 solid phase extraction cartridge (Silicycle™ brand, 500 mg). This C8 cartridge was prepared before use by passing 15 mL of HPLC grade methanol through the cartridge followed by 20 mL of HPLC grade water. The fungal extract was observed to adhere to the stationary phase by a color change. The cartridge was then washed with 20 mL of HPLC grade water under vacuum in a solid phase extraction manifold. Air was drawn through the cartridge for 5 minutes after loading to remove excess water. The compounds retained on the cartridge were eluted by adding 5 mL of HPLC grade methanol and collecting to eluant in a three-dram vial. One mL of this eluant was placed in a GC vial which was capped and analyzed using the temperature program and process described above. Dr. James Harper of BYU performed these analyses.

Example 2. Storage of Isolated Truffle Species

One critical requirement for the domestication of these truffle fungi is the ability to successfully store them for recovery and future use. Many techniques are available for this purpose and several of the standard procedures were tested. The isolated truffle species were tested and the techniques described below resulted in successful storage of these isolated cultures.

1. Storage in Sterile Water at Refrigerator Temperatures.

Two- to three-week-old cultures of each of the truffle fungi, growing on PDA potato dextrose agar, had the surface of the agar plate scraped with a bacterial loop. The spores and hyphal fragments picked up by the loop were then placed by shaking into a small vial containing about 1 ml of sterile distilled water. The vial was then capped and placed at 3° C. for various time periods. Subsequently, a loop was reinserted into the spore suspension and spread over the surface of a freshly prepared plate of PDA. The isolates of *T. melanosporum* and *T. borchii* showed growth on the plates within 2 days after having been stored for over 1 year. The isolates of *T. aestivum*, T. *magnatum*, *T. uncinatum* and *Imaia* spp. all showed positive growth after storage for 3 months and even up to 1 year. This technique is a promising one for keeping viable cultures of the truffle fungi.

2. Storage of Infested Grains at −80° C.

Once a truffle fungus has been growing on PDA for several weeks, a group of 20-30 sterile (autoclaved) barley or rice seeds were placed on the agar surface over the growing fungal culture which allowed the seeds to become infested with the fungus. The seeds had been prepared by adding water at 1 volume seeds to 1 volume water and then autoclaved followed by cooling and re-autoclaving with the addition of 0.5 vol water to 1 vol of grain. Two cycles of autoclaving were needed to destroy the spore forming bacteria commonly associated with them. The sterilized grains were incubated on the truffle fungus infested plate for two to three weeks and then placed in cryo-vials, appropriately labeled, at −80° C. for extended periods. The tested truffle fungi were readily recovered from this storage condition for a minimum of 1 year after placement at this storage temperature.

3. Storage of Infested Dried Grain at 22° C.

The infested seeds, above as outlined, instead of being placed at −80° C. were simply removed from the PDA plate and placed in an empty plastic Petri plate and allowed to dry at 22° C. The plates were then wrapped with parafilm and stored at 22° C.

Intermittently, seeds were removed and placed on regular PDA to check for fungal viability. Each of the tested truffle fungi could withstand drying and storage at room temperature for at least one year or longer.

Other observations on the storage and durability of the truffle fungi at various temperatures revealed the following:

a. Infested seeds can also be stored at −18 to −20° C. and the fungi remain viable for extended periods. They also remain viable if removed from storage, thawed and refrozen.

b. Infested seeds, when placed at −80° C. then removed and thawed and refrozen, also remain viable. This is not a common observation for most fungi as they expire if frozen—thawed—and refrozen.

c. The fungi can stand heat exposures of many minutes of up to 35 to 50° C.

d. The truffle fungi generally expires at 65 to 70° C. with a two-hour exposure.

Ultimately, each of the truffle fungi were grown on sterile barley seeds for several weeks and then these colonized seeds were transferred to cryo-vials and stored at −80° C. and they all can be successfully stored under these conditions for extended periods. They are all successfully stored and preserved in the Montana State University culture collection and in the collection of the Black Boar Truffle Co.

Example 3. Use of Isolated Truffle Fungi Species

Pure cultures of many of the truffle fungi described above have been developed available. Each of these can now be grown on artificial and natural media, as well as a wide range of natural products such as grains, nuts, and fruits which will make available an untold number of possible novel products each with a different set or combination of flavors. The truffle fungus will potentially convert the natural products in the grain or fruit into other compounds that have interesting and useful flavored substances lending novelty to the fermentation process and new product development.

Furthermore, the novel truffle fungus isolation procedure disclosed above will readily allow for the recovery of numerous local strains of the fungus which may prove useful in finding stand alone and unique natural foods. In this case novel flavors can be created by growing the local truffle strains of the fungus on grains, nuts, powders, floral parts or mixtures of such natural plant products.

The technique for culturing these fungi on seeds and grains is mostly done by solid state fermentation as follows:

1. Use 1 liter volume of the product such as rye, rice or barley seeds water
2. Add water at 0.6 up to 3.0 liter (depending upon the seeds being used)
3. Then add 5 g glucose, 1 g peptone and 2 g of yeast extract stir liberally.

Various sized Erlenmeyer or other specially designed glass flasks may be used to carry out the fermentation process. The truffle fungi prefer not to grow in a submerged state, therefore the amount of water present in the final mixture is critical to fungal growth and development. However, in most cases for solid-state mass production, the mixture is placed in a plastic bag having a 1.5- to 2-inch-wide portal that is plugged with a foam cylinder and covered with a sheet of aluminum foil after inoculation. Autoclaving is done for 30-40 min. in order to achieve complete sterilization of the contents. Upon cooling the bag is then inoculated with the spores and mycelium of one of the truffle fungi by placing them though the opening port in the bag. One way to inoculate the bag with spores is, for example, by inoculating with 10-20 *Tuber* spp. infested barely seeds that had been incubated on a PDA plate for several weeks. The spores and mycelium then grow throughout the contents of the plastic bag. The bag is incubated under still conditions in the dark at 19-20° C. for 4-6 weeks with periodic mixing of the contents by handling. A temperature lower than that of normal room temperature is preferred i.e., 19-20° C.

Figure 12:
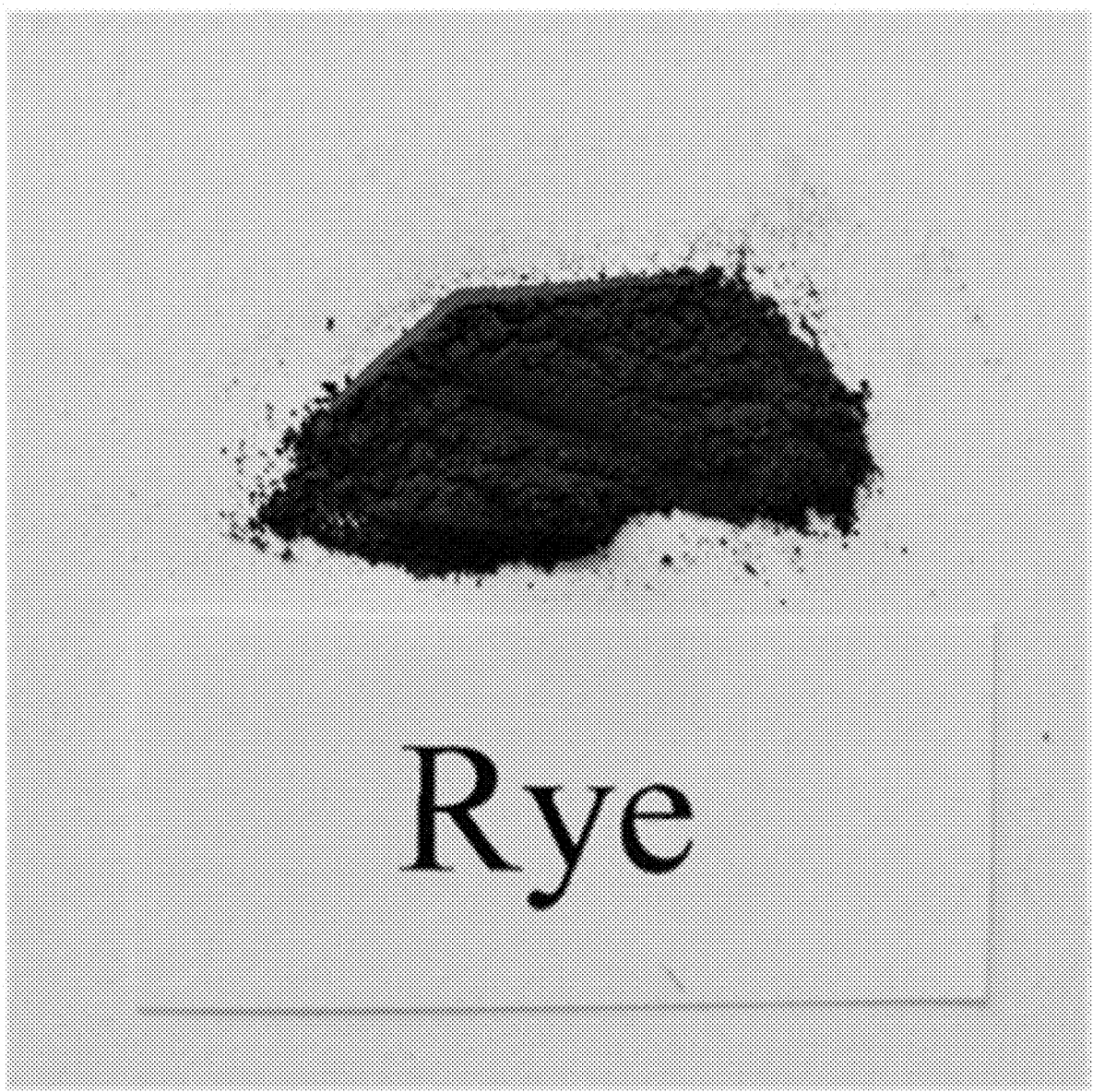
FIG. 12 is an image illustrating the rye truffle powder made from the fermentation of the black truffle on sterile rye seeds. Powders like this are the main products of the truffle fungi fermentation processes.

The contents of the bag may be treated differently, depending upon what is being fermented. Initially, various grains/seeds including wheat, rice, rye, lentils and barley were fermented utilizing the first truffle fungus that was successfully isolated—*Tuber melanosporum*. After fermentation the seeds were removed and placed on a flat metal pan and heated at 60° C. in order to effectively dry the product. The seeds are then ground to a fine powder and thus made ready as a product for testing. The dark powder rye truffle product (FIG. 12) is now widely sold as an additive to salt (truffle salt) and olive oil (truffle oil) and finished bagged products such as truffle potato chips (Table 4). The development of other powders resulting from the fermentation of this truffle fungus on various other seeds has been done and the products have been tested and are being made ready for the marketing process (Table 4). This includes the novel black truffle products made with lentils, brown rice, wheat and barley as substrates for the fungus. Finally, soybeans were used as a substrate for the black truffle fungus and both the liquid (filtrate from the fermentation process) and the dried powder produced a basic classic truffle flavored product. The liquid has the potential of being labeled as truffle soy sauce after the famous Japanese soy sauce but with the added truffle flavoring notes (Table 4). The various powders made from these grain fermentations may be used for flavorings for hot drinks, salts, oils, vinegars, as well as for seasonings for meats, baked goods, eggs, and soups. Appropriate testing has been done to demonstrate the practical uses of each of these plant sourced fermentation powders.

As an example of the utility of the black truffle-pecan mash is the production of a mixture that is tasty and has a multitude of uses. The product is made by making a 50:50 v/v mixture with honey which can be used as a novel biscuit, toast or waffle spread. Modifications of the mixture can be made by varying the ratio of honey to the pecan/truffle fermentation product down to the 5% level still with acceptable taste results. A taste test of the 50/50 mixture was given to a panel of local adults and their responses showed overwhelmingly that they thought the product was tasty and novel (Table 6). Two respondents did not like the truffle smell and taste, and this is a perfect match to the general population i.e. approximately 20% who feel likewise with truffle products. A similar mixture was made with English walnuts yielding and entirely different tasting dried product with both the black and white truffle fermentation products. Different ratios of the honey to the nut/truffle product have also been made and tested with comparable results. Other possibilities include hazelnuts, peanuts, almonds, brazil nuts, cashews, pistachios, macadamia, chestnut, and cacao.

TABLE 4

Fermentation of the black truffle (*T. melanosporum*) on various substrates and the products and uses derived thereof. It is to be noted that each of these products has its own distinct odor and flavor. A multitude of uses are currently and potentially possible.

| Plant source or nutrient source | Final product | Uses of product | Public acceptance And sales |
|---|---|---|---|
| Rye | Dark brown powder | Truffle salt, truffle olive oil, potato chips, general flavoring | Yes-worldwide marketing and sales for uses indicated |
| Barley | Light brown powder | Potential for breads, biscuit mixes, general flavoring -maybe pizzas coffee and tea flavoring | In development |
| Wheat organic (Kamut) | Light brown powder | A flavoring substance with a mild truffle taste For eggs, meats, drinks | In development |
| Lentil | Brown powder | Used to flavor soups, drinks, salts and oils | A novel product with multiple uses. |
| Brown rice | Brown powder | Food flavoring as per the rye product above and coffee flavoring additive. Maybe a better substrate for the fungus than the rye | Tested for many uses and accepted as a potential product as per the rye product above |
| Soybeans | Liquid from fermentation/ brown powder from dried fermentation product | Mild but distinctive truffle smell and taste Truffle flavoring agents | In development and may have potential as products but will require research |

Besides grains there are a plethora of other seeds, and nuts that may serve as potential fermentation sources for the truffle fungi. To this end, a representative list of commonly available natural products was tested for their abilities to support the growth of the various truffle fungi and make novel useable and desirable food products. In the case of nuts and seeds the fermentation was carried out as described above in the grain testing experiments. The initial tests were done with pecans incubated with the black truffle fungus; the final product was a viscous liquid mash like product which could be utilized in a multitude of ways. The white truffle fungus was also fermented in this manner. The final fermentation product could also be dried and ground to a powder for use (Table 5). However, the viscous liquid product, taken directly from fermentation, could ideally be used as a dressing for buns, biscuits, toast, waffles or crackers and a plethora of other foods especially when mixed with honey or maple syrup for a sweetened version of the truffle/pecan mixture.

These results provided encouragement to proceed with other nuts and seeds as per Table 5.

As outlined above many other nuts and seeds were fermented using the exact fermentation formula and conditions as described for pecans and walnuts as shown in Table 5. As an example, coffee beans were fermented for 6 weeks on sterile coffee beans and the sugar/peptone mixture, and the final dried product (as above) was ground and mixed at different levels with standard coffee bean powder and made into a delicious drink. The final product was made by mixing either 10% or 20% of the truffle coffee bean powder with 80 to 90% of regular coffee beans to make the brew for the best truffle/coffee taste. Also, the addition of cream to the coffee bean mixture resulted in a wonderful tasting truffle/coffee/latte (Table 5). The same process has been applied in making a truffle cocoa mix using one or more of the truffle powders or mash products to be mixed/added to standard cocoa powder or powder mixture to produce the drink (Table 5). In each of the nut/bean cases novel products can be made as candies mixed with chocolate, white chocolate or other sugary substances to yield novel tasting products each of which can be labeled with the truffle species used to make the product. Such is the case with the hazelnut whose taste was distinctly unique from the other nut products (Table 5).

In each of these examples done with the black truffle, the process can be substituted with any of the other truffle fungi that have been isolated by the methods described and subsequently applied to the fermentation schedules as outlined for the black truffle (Table 4). Basically, totally new products can be made because the flavoring is different with each of the truffles. Virtually all the major truffle species have been isolated in this manner and testing has shown that they do grow on natural products such as seeds and beans as per the *T. melanosporum* (black truffle). Furthermore, it is extremely likely that individual truffle isolates will have important subtle flavoring properties that are unique to them which makes the isolation and acquisition of individual truffle strains even more important.

product yielded a unique savory-umami tasting/smelling product that represents a total all around seasoning for roasts, and steaks and seafoods. It was evaluated by a well-trained chef and its use for tapenades was also suggested (Table 5). Interestingly, the pine nut product yielded a very spicey almost peppery tasting product that could be used in salad dressings and other flavoring products (Table 5). Likewise, the fermentation filtrate (white truffle) as well as the powder from the soybean test yielded nice umami-like products (Table 5).

Both the white and brown long grain rice products with the black truffle fungus yielded a black powder product for use as a general flavoring agent. The rice as a substrate has the advantages of being relatively uncontaminated and easier and quicker for the truffle fungi to ferment based on the ease and shorter times for the fungi to grow and develop on these substrates. Both the burgundy and the whitish truffle fungi did yield potential mild flavoring products on white long grained white rice, but no products could be

TABLE 5

| Plant source | T. melanosporum | T. borchii | T. uncinatum | T. magnatum | T. aestivum |
|---|---|---|---|---|---|
| White rice long grain | Dark brown powder for salt and oil flavorings | A nice mild flavored product as a seasoning | A potential mild flavoring product | A nice sweetened product with A special nutty taste-potential flavoring | No product |
| Brown rice Long grain | Dark brown powder for truffle flavorings | | A novel flavored sweet product for a multitude of flavorings | A very nice intense fruity/truffle flavor# | — |
| Pecan mash or Pecan powder | Mixed with honey or maple syrup -novel food products* | | | Mix with honey or maple syrup - nutty/mild truffle taste at 10%* | |
| Walnut English-mash or powder | Mixed with honey for a unique nut product for toppings, spreads | | | Mix with honey or maple syrup - nutty/mild truffle taste at 10% | |
| Hazelnut mash+ | Mixed with honey or maple syrup for toppings | | | | |
| Pine nut | Dried product with novel tangy-peppery taste | | | | |
| Mustard | A taste better than mustard with nice truffle flavored product-tangy | | | Very unique mild truffle taste- no bitterness-a novel mustard product- | |
| Cacao roasted | Dried powder tastes like chocolate but no bitterness | | | | |
| Coffee beans+ | Mixed up to 10% with regular coffee, yields truffle/coffee | | | | |
| Sunflower+ | For flavorings has the standard truffle odor and taste | | | For tapenades, - umami taste Great Seasoning | |
| Sesame | A remarkably novel spicy tasting powder for seasonings | | | | |
| Soybean Powder and/ or liquid fermentation products | See table 3 | | | Fermentation liquid, as well as powder- umami flavor | |

*See table for subject evaluation ratings for this product as an example of how evaluations of these novel products were performed (Table 6). This fungus made useable large truffle like structures in this culture.
+These are very promising and very surprising novel products.

A totally unexpected result was obtained when the fermentation product of the white truffle fungus had been grown on sunflower seeds (Table 5). The dried fermentation obtained from the summer truffle (Table 5). Finally, mustard sauce made from the white and black truffle fermentation products yielded totally novel tasting mustards with white and black truffle tasting overtones with totally unique very distinctive appetizing flavors (Table 5).

TABLE 6

Taste panel evaluation of the black truffle pecan honey syrup product mixed 10-20% by weight with honey.*

| Person's designation | Novelty of product 1-10 low to high | Would you buy it if available reasonably | Added comments |
|---|---|---|---|
| 1 | 7 | Yes | Chocolate taste |
| 2 | 7 | Yes | Different nice taste |
| 3 | 8 | Yes | Hint of chocolate |
| 4 | 7.5 | Yes | Chocolate taste |
| 5 | 6.5 | Yes | Toffee -like |
| 6 | 8 | Yes | Chocolate- like |
| 7 | 8 | Yes | Novel taste -nice |
| 8 | 8 | Yes | Very good taste |
| 9 | 8 | Yes | Excellent taste |
| 10 | 7 | Yes | Novel taste-great! |
| 11 | 0 | No | Bad smell |
| 12 | 10 | Yes | Great, wonderful |
| 13 | 10 | Yes | Perfect treat taste |
| 14 | 8 | Yes | Novel, interesting |
| 15 | 8 | Yes | Very nice taste |
| 16 | 0 | No | Intolerable taste |
| 17 | 7 | Yes | Nice taste- surprise |

All subjects were adults living in Bozeman and many were professionals or student volunteers. They had many suggestion for the use of the product i.e. for toast, waffles, and a spread for fancy crackers. The two outliers reflected the normal human average of about 20% of the population who do not like the odor or taste of truffles or truffle products.

Besides growing the truffle fungi on seeds (grains) and nuts, a wide variety of berries and fruits were fermented into juices/drinks with novel tasting results (Table 7). In each case the following set up was done to carry out the fermentation and evaluation processes:
1. Use 150 g of fruit or berry product that was liberally smashed.
2. Added 0.25 g of peptone
3. Added 100 ml of water Incubated for 2 weeks at 19-20° C. and then the contents were filtered through 4 layers of coffee filter paper to yield mostly a clear product. Taste testing was done using at least a minimum of three subjects doing an evaluation ranking of 1-10 based on flavor, sweetness, uniqueness, desirability, and overall potential as a novel drink perhaps for use as an aperitif or digest if. The data were subjected to averaging and standard deviation of the mean (Table 7). It is to be noted that with the Thompson seedless grapes each of the truffle fungi yielded a better tasting product than the liquid product having not supported fungal growth (control) (Table 7). The same was true with all products having a grape additive including red seedless or black seedless alone, and/or blackberry alone or with any of the grape additives (Table 7). The dried cherry drink with either the black or the white truffle fungi was also superior. However, generally the golden kiwi did not yield any product with outstanding potential (Table 7). Interestingly, the yellow mango drinks with market potential were the black, whitish and summer truffle fungi (Table 7). Likewise, the red raspberries and huckleberries also yielded excellent drink products especially with the black truffle fungus, but the burgundy truffle gave excellent results with the Thompson seedless grapes, the dried cherries as well as the huckleberries (Table 7).

Table 7—Juice evaluation of the truffle fungal fermentation of various berries/fruits after incubation for 2 weeks at 22 C and then harvested by filtering 4 layers of a coffee filter. Evaluation was done by at least 5 people who rated the juice by flavor, sweetness, uniqueness, desirability and overall potential as a novel drink. The scale was 1 lowest and 10 highest.

| | Truffle Fungus Used in Fermentation | | | | | |
|---|---|---|---|---|---|---|
| Plant Source | T. melanosporum | T. borchii | T. aestivum | T. uncinatum | T. magnatum | none |
| Thompson Seedless grapes | 9.5 ± 0.4 | 4.5 ± 0.4 | 4.0 ± 0 | 7.8 ± 1.2 | 7.3 ± .7 | 1.5 ± 0 |
| Red Seedless grapes | 9.2 ± 0.4 | — | — | — | 5.4 ± 1.0 | 1.5 ± 0 |
| Blackberry with Red Seedless Grapes | 8.0 ± 0.7 | — | — | — | — | 3.5 ± 0.5 |
| Blackberry | 6.5 ± 0.5 | 1.0 ± 0 | — | — | 2.0 ± 0 | 2.3 ± 0.5 |
| Blueberry | 7.0 ± 0 | 1.0 ± 0 | 2 ± 0.8 | 3 ± 1.4 | 3.3 ± 1.7 | 2.5 ± 0.5 |
| Blueberry with Black seedless grape 1:1 | 7.5 ± 0.4 | — | — | — | — | 3.5 ± 0.5 |
| Black seedless grapes | 7.0 ± 0 | — | — | — | — | 2.0 ± 0 |
| Dried cherries Montmorency | 9.7 ± 0.5 | — | — | 9.0 ± 0 | 7.0 ± 0 | 7.0 ± 0 |
| Golden Kiwi | 2.2 ± 1 | 1.0 ± 0 | 1.0 ± 0 | 1.3 ± 0.3 | — | 1.5 ± 0.5 |
| Yellow mango | 6.7 ± 0.5 | 6.3 ± 0.9 | 5 ± 2.2 | 0.7 ± 0.5 | 1.3 ± 0.9 | 4.3 ± 1.2 |
| Red raspberries | 9.5 ± 0.5 | | | | | 6.4 ± 0.8 |
| Freshly harvested huckleberries | 7.5 ± 0 | — | — | 7.0 ± 0.5 Different taste | 6.3 ± 0.3 Different taste | 5 ± 0.8 |

*Dried Montmorency dried cherries - fermentation done without the yeast extract since it caused some off flavoring in the first test.

E. *Tuber* Spp. Growth on a Special Medium to Produce Mycelium Alone

Now, if one wants a relatively pure fermentation product to be mycelium alone and not mixed with any major seed or nut or natural plant product such as seed coats or other unfermented natural seed products the following procedures are used. A fermentation process is done using only a liquid medium in still culture in order to produce an intact mycelium.

1. 0.5 g glucose
2. 0.2 g peptone
3. 0.4 g yeast extract
4. 10 grams of finely ground white rice powder
5. 100 ml of water (this amount may vary depending upon water loss at the time of autoclaving). Only a thin layer of water is wanted on the flask bottom as the fungus does not grow well in submerged culture conditions.

Place the mixture in a 2-liter flask and add the truffle fungus. Incubate at 19-20° C. with no stirring or mixing of the flask contents during the incubation process. In all cases a very nice solid mycelium develops that can be dried, and ground into a powder or sold as an intact truffle mycelium itself. For example, mycelium may be harvested by filtration and dried at 60° C. The dried-dark mycelium can then be ground into a powder and used accordingly. Also, the intact mycelium maybe be rolled as per a tortilla, and/or dried to yield a final product.

This process may take 4-8 weeks of fermentation on any number of modifications of the broth medium formula including the supplementation with methionine to yield a different set of sulfur containing flavoring products especially with the black and the white truffle fungi. The mycelium is then harvested by simply letting it slide out of the flask and then processed by drying or rolling it into tube-like shape.

F. Truffle Inoculum for Trees Planted in the Field for Wild-Truffle Production

To test the use of infested grains to inoculate trees in the field, 1 year old dried infested barely seeds (with *T. melanosporum*) were placed in 50 grams of loamy soil contained in a Petri plate at 22° C. The soil was then dampened with sterile water and the seeds observed as a function of time. After 3 days of incubation there was an abundance of synnemata and infectious conidiospores produced on each of the infested seeds as per visual and microscopic observations (FIG. 13). Artificially infecting the tree roots should be done over a process of several days in which dampened roots are placed with an abundance of infested barley seed prior to planting under field conditions.

Experimentally, it was determined what might be the best truffle fungal inoculum by growing *T. melanosporum* on long grained white rice with the added 5 grams glucose/1 gram peptone/2 grams yeast extract for 6-8 weeks in an aqueous suspension of 1 volume of rice per 4 vol of water with frequent stirring and mixing (same formula as above-page 26). This fungal suspension (3 vol-300 ml) was added with mixing with 5 vol (500 ml) of previously autoclaved MiracleGro® brand soil planting mixture or other organic soil mixtures. The fungal soil mixture was then placed in plastic bags and stored under diverse conditions. Basically, this would allow for the determination of which conditions would be best for storage, and shipment of a viable inoculum product.

1. A portion of the fungal soil mixture was air dried in a chemical hood at 22° C. for two days and then stored at 22° C. in a plastic bag.
2. A portion of the mixture was stored at room temperature at 22° C. in a plastic bag.
3. A portion of the mixture was stored at 3° C. in a refrigerator in a plastic bag.
4. A portion was stored a −20° C. in a plastic bag which is the freezer compartment temperature of a standard refrigerator.
5. Then a portion was stored at −80° C. in a special laboratory freezer.

Figure 9:
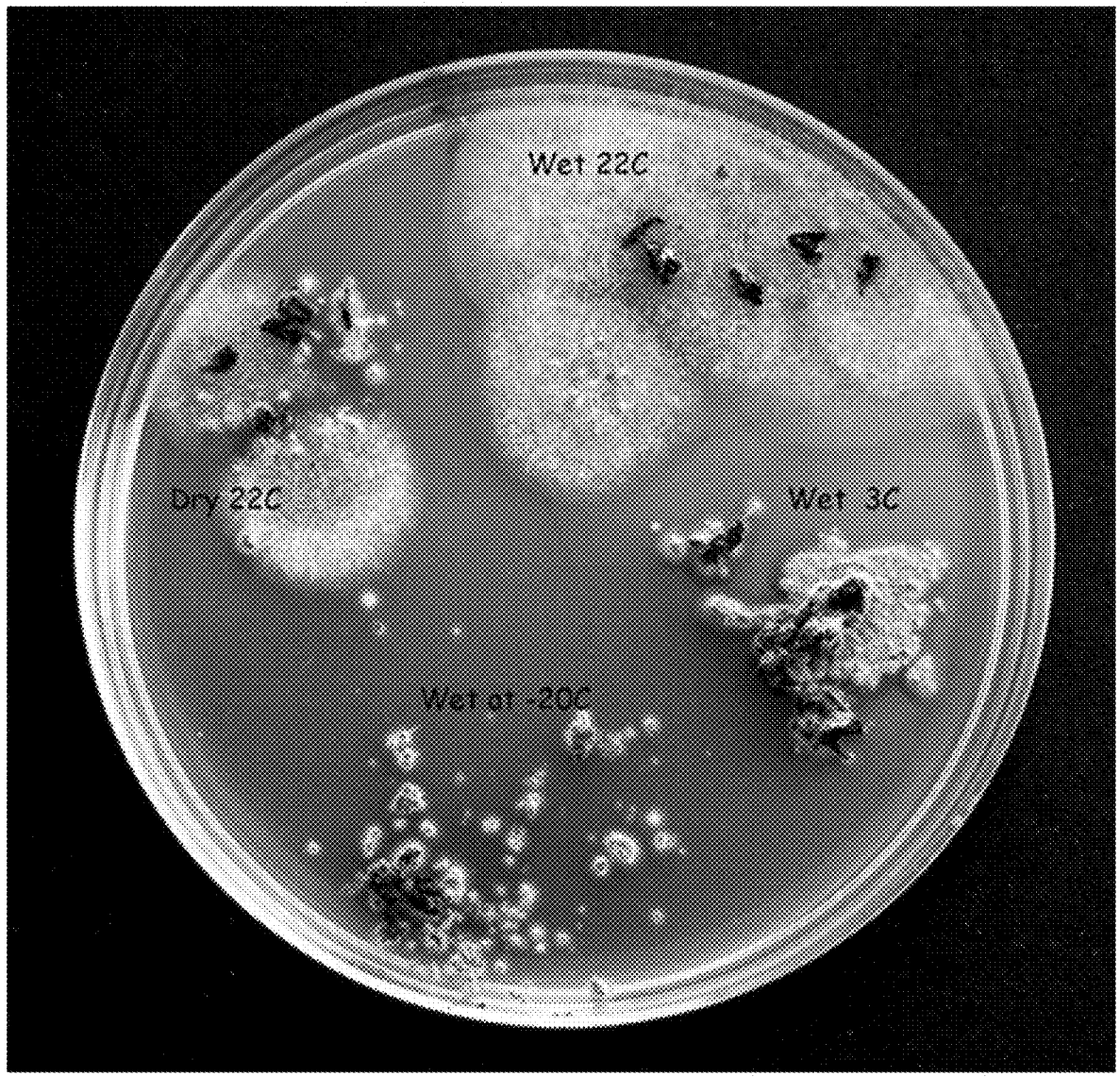
FIG. 9 is an image representation of an experimental determination of the best storage conditions of the rice fermentation/soil mixture as an inoculum for trees with *T. melanosporum*. Both the wetted mixture held at 3° C. as well as −20° C. contained no obvious bacterial or fungal colonies contamination whereas, the both the wet and dry preparations held at 22° C. displayed significant contamination.

After 1 week in each of these conditions a few mg of the contents of each bag were aseptically taken and placed upon a distinct location on a PDA plate to determine the viability of the truffle fungus and the degree of microbial contamination. It can be seen (FIG. 9), after a three-day incubation, that both the dried preparation as well as the wet sample held at room temperature exhibited contamination of the "yellowish"-black truffle fungus by other fungi which is not acceptable. However, the preparations held at both freezing temperature −20° C. and at regular refrigerator temperature of 3° C. there was virtually no contamination and the truffle fungus flourished and remained viable. This was also true of the preparation held at −80° C. Thus, it appears that any of these methods for truffle fungal inoculum preparation would be useful as a product developed for marketing to those interested in the field production of truffles, but the −80° C. method would prove too costly to implement and provide for shipping. The dried product would also be useful as a product, but the drying process would need to be done under aseptic conditions since the fungus (yellowish growth) is present but has contaminating fungi (FIG. 9).

Figure 10:
FIG. 10 is an image representation showing an oak root section two weeks after it was inoculated with the *T. melanosporum* inoculum mixture, mini-truffles began to form, as seen from the whitish tuffs of mycelium that are forming on the oak root section.

Finally, as a check to learn if the *T. melanosporum*/soil mixture (at −20° C. and −3° C. would be effective in producing truffle-like bodies in nature, experiments were carried out with the mixture placed on oak roots. White oak roots of 1-2-year-old trees were obtained freshly harvested from a forest in Virginia. The roots were sawed into cross sections about 2-3 mm thick. They were then sterilized by autoclaving for 20 min. as well as only surface sterilized by treating with 70% ethanol and then flaming for several seconds until the alcohol was burnt off the tissues. This latter process was repeated 3 times. The root sections were then placed on water agar and carefully inoculated with rubbing of 1-2 mg of the fungus/soil mixture on the surface of the root sections having been stored at either −3° C. or −20° C. After two weeks on both the autoclaved as well as the surface treated oak root sections small mini-truffles (0.5-1.0 mm) appeared on the surfaces of all root sections (FIG. 10). These observations strongly suggest that the fungus/soil mixture (under either of these temperature regimes) would serve as a viable and possibly a better alternative for the field inoculation of host trees for wild truffle production. But in addition, the mixture was added to water and place down several 3-4 cm holes made with an iron bar in the root region of a white oak tree growing in the Bozeman, Mt., area. In this case the results may not be known for several years, but the application methodology works perfectly.

REFERENCES CITED AND INCORPORATED BY REFERENCE

1. Nowak, Z. 2015. Truffle: A Global History. Reaktion Books. 128P.
2. De Aza, C., et al., 2022. Fungal and bacterial communities in *Tuber melanosporum* plantations from northern Spain. Forests 13: 385-
3. Cullere, L. et al., 2009. Characterization of aroma active compounds in black truffles (*Tuber melansporum*) and summer truffles (*Tuber aestivum*) by gas chromatography. olfactometry. Food Chemistry 122-300-306.
4. Strobel, G. A., Dirksie, E., Sears, J., and Markworth, C. 2001. Volatile antimicrobials from a Novel Endophytic Fungus. Microbiol. 147: 2943-2950.

5. Saxena, S and Strobel, G. A. 2021. Marvelous *Muscodor* spp.: update on their biology and applications. Microbial Ecology 82: 5-20.
6. Mitchell, A. M. Strobel, G. A., Moore, E., Robison, R., and Sears, J. 2010 Volatile antimicrobials from *Muscodor crispans*. Microbiology 156: 270-277.
7. Urban, A., et al., 2004. Molecular studies on terricolous microfungi reveal novel anamorph of two *Tuber* species. Mycol. Rev 108: 749-758.
8. Iotti, M. et al., 2002. Morphological and molecular characterization of mycelia of some *Tuber* species in pure culture. New Phytologist 155: 499-505.
9. White, T. J. (1990) Amplification and Direct Sequencing of Fungal Ribosomal RNA Genes for Phylogenetics. In: PCR Protocols, a Guide to Methods and Applications, 315-322.
10. Mustafa, A. M. et al., 2020. An overview of truffle aroma and main volatile compounds. Molecules. 25: 5948; https://doi.org/10.3390/molecules25245948
11. Vahdatzaheh, M., et al., 2015. The Role of the Microbiome of Truffles in Aroma Formation: A Meta-Analysis Approach. Appl. Environ. Microbiol. 81: 6946-6952.

We claim:

1. A method of growing truffle fungi comprising the steps of:
    obtaining a spore-producing fruiting body of an ascomycetous fungus from soil, wherein the ascomycetous fungus is a *Tuber* spp. or an *Imaia* spp.;
    scraping the inside of the spore-producing fruiting body of the ascomycetous fungus to collect a fruiting body sample;
    placing the fruiting body sample on a first surface comprising a first nutrient substrate, wherein the first nutrient substrate comprises:
        a simple sugar;
        a botanical isolate; and
        agar;
    incubating the fruiting body sample on the first nutrient substrate with an antimicrobial volatile mixture until mycelium formation, wherein the antimicrobial volatile mixture is derived from the volatile organic compounds produced by *Muscodor* crispans, and wherein the presence of mycelium indicates new fungal growth; and
    transferring the new fungal growth into a second surface comprising a second nutrient substrate to obtain a pure culture of the ascomycetous fungus.

2. The method of claim 1, wherein the *Tuber* spp. is selected from a group consisting of: *Tuber melanosporum, Tuber magnatum, Tuber aestivum, Tuber uncinatum, Tuber borchii, Tuber macrosporum, Tuber gibbosum, Tuber oregonense*, and *Tuber lyonii* syn. *Texense*.

3. The method of claim 1, wherein the antimicrobial volatile mixture comprises: Propanoic acid, 2-methyl-, methyl ester; Ethanol; Acetic acid, 2-methylpropyl ester; Propanoic acid, 2-methyl-, 2-methylpropyl ester; 1-Propanol, 2-methyl-; 2-Butenal, 2-methyl-, (E)-; 1-Butanol, 3-methyl-, acetate; Propanoic acid, 2-methyl-, 2-methylbutyl ester; 1-Butanol, 3-methyl-; Propanoic acid, 2-methyl-, or isobutyric acid; and Acetic acid, 2-phenylethyl ester.

4. The method of claim 1, wherein the second nutrient substrate is liquid.

5. The method of claim 1, wherein at least the first nutrient substrate is potato dextrose agar.

6. The method of claim 4, wherein the second nutrient substrate is potato dextrose broth.

7. The method of claim 1, wherein at least the first nutrient substrate is pecan agar.

8. A method of growing mini truffles comprising:
    obtaining a spore-producing fruiting body of an ascomycetous fungus from soil, wherein the ascomycetous fungus is a *Tuber* spp. or an *Imaia* spp.;
    scraping the inside of the spore-producing fruiting body of the ascomycetous fungus to collect a fruiting body sample;
    placing the fruiting body sample on a first surface comprising a nutrient substrate, wherein the nutrient substrate comprises:
        a simple sugar;
        a botanical isolate; and
        agar;
    incubating the fruiting body sample on the nutrient substrate with an antimicrobial volatile mixture until mycelium formation, wherein the antimicrobial volatile mixture is derived from the volatile organic compounds produced by *Muscodor* crispans, and wherein the presence of mycelium indicates new fungal growth;
    transferring the new fungal growth into second surface comprising the nutrient substrate to obtain a pure culture of the ascomycetous fungus;
    incubating the pure culture with fruit, nut, grain, or a portion thereof for at least week to produce an inoculated botanical sample; and
    placing the inoculated botanical sample on a third surface comprising the nutrient substrate to produce mini-truffles.

9. The method of claim 8, wherein the third surface comprises pecan agar.

10. A method of growing mini-truffle comprising:
    obtaining a spore-producing fruiting body of an ascomycetous fungus from soil, wherein the ascomycetous fungus is a *Tuber* spp. or an *Imaia* spp.;
    scraping the inside of the spore-producing fruiting body of the ascomycetous fungus to collect a fruiting body sample;
    placing the fruiting body sample on a first surface comprising a nutrient substrate, wherein the nutrient substrate comprises:
        a simple sugar;
        a botanical isolate; and
        agar;
    providing to the fruiting body sample on the nutrient substrate;
    incubating the fruiting body sample on the nutrient substrate with an antimicrobial volatile mixture until mycelium formation, wherein the antimicrobial volatile mixture is derived from the volatile organic compounds produced by *Muscodor* crispans, and wherein the presence of mycelium indicates new fungal growth;
    transferring the new fungal growth into second surface comprising the nutrient substrate to obtain a pure culture of the ascomycetous fungus;
    incubating the pure culture with fruit, nut, grain, or a portion thereof for at least week to produce an inoculated botanical sample;
    placing the inoculated botanical sample in a sugar solution for at least a week to produce inoculated sugar solution and incubating inoculated sugar solution on a third surface comprising the nutrient substrate to produce mini-truffles.

11. The method of claim 10, wherein the third surface comprises potato dextrose agar or pecan agar.

12. The method of claim 11, wherein the sugar solution is honey or maple syrup.

13. A method of growing a known species of truffle, the method comprising:
obtaining a spore-producing fruiting body of an ascomycetous fungus from soil, wherein the ascomycetous fungus is a *Tuber* spp. or an *Imaia* spp.;
scraping the inside of the spore-producing fruiting body of the ascomycetous fungus to collect a fruiting body sample;
placing the fruiting body sample on a first surface comprising a nutrient substrate, wherein the nutrient substrate comprises:
a simple sugar;
a botanical isolate; and
agar;
providing to the fruiting body sample on the nutrient substrate;
incubating the fruiting body sample on the nutrient substrate with an antimicrobial volatile mixture until mycelium formation, wherein the antimicrobial volatile mixture is derived from the volatile organic compounds produced by *Muscodor* crispans, and wherein the presence of mycelium indicates new fungal growth;
transferring the new fungal growth into second surface comprising the nutrient substrate and a sterile medium selected from the group consisting of: nut or a portion thereof and a grain or a portion thereof to obtain an inoculant;
combining sterile water with the inoculant at a volume ratio 1 part inoculant to 4 parts water to produce a suspension;
mixing the suspension with a soil mixture to produce a fungal soil mixture; and
applying the fungal soil mixture to a plant root or a portion thereof.

14. The method of claim 13, wherein the fungal soil mixture is air dried and stored at 3° C.

15. The method of claim 13, wherein the fungal soil mixture is stored at −20° C.

16. The method of claim 13, wherein the fungal soil mixture is stored at −80° C.

17. The method of claim 13, further comprising the step of mixing the fungal soil mixture with the soil in the area where roots of desired host trees are growing.

18. The method of claim 1, wherein the second nutrient substrate is the same as the first nutrient substrate.

19. The method of claim 2, wherein the antimicrobial volatile mixture comprises:
Propanoic acid, 2-methyl-, methyl ester; Ethanol; Acetic acid, 2-methylpropyl ester;
Propanoic acid, 2-methyl-, 2-methylpropyl ester; 1-Propanol, 2-methyl-; 2-Butenal, 2-methyl-, (E)-; 1-Butanol, 3-methyl-, acetate; Propanoic acid, 2-methyl-, 2-methylbutyl ester; 1-Butanol, 3-methyl-; Propanoic acid, 2-methyl-, or isobutyric acid; and Acetic acid, 2-phenylethyl ester.

\* \* \* \* \*